(12) United States Patent
Barker et al.

(10) Patent No.: US 10,357,629 B2
(45) Date of Patent: Jul. 23, 2019

(54) RESPIRATORY ASSISTANCE APPARATUS

(71) Applicant: Fisher & Paykel Healthcare Limited, Auckland (NZ)

(72) Inventors: Dean Antony Barker, Auckland (NZ); Mikael Douglas Stewart, Auckland (NZ); Peter Geoffrey Hawkins, Auckland (NZ); Kevin Peter O'Donnell, Auckland (NZ); Russel William Burgess, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 157 days.

(21) Appl. No.: 14/390,358

(22) PCT Filed: Apr. 5, 2013

(86) PCT No.: PCT/NZ2013/000059
§ 371 (c)(1),
(2) Date: Oct. 2, 2014

(87) PCT Pub. No.: WO2013/151447
PCT Pub. Date: Oct. 10, 2013

(65) Prior Publication Data
US 2015/0059745 A1    Mar. 5, 2015

Related U.S. Application Data

(60) Provisional application No. 61/620,595, filed on Apr. 5, 2012.

(51) Int. Cl.
*A61M 16/00* (2006.01)
*A61M 16/10* (2006.01)
(Continued)

(52) U.S. Cl.
CPC ...... *A61M 16/109* (2014.02); *A61M 16/0003* (2014.02); *A61M 16/0051* (2013.01);
(Continued)

(58) Field of Classification Search
CPC .............. A61M 16/109; A61M 16/003; A61M 16/0051; A61M 16/0875; A61M 16/20;
(Continued)

(56) References Cited

U.S. PATENT DOCUMENTS 1,269,599 A    6/1918  Haber
1,570,781 A    6/1926  Ruben
(Continued)

FOREIGN PATENT DOCUMENTS

AU    2014202639        12/2014
CN    102105189 A       6/2011
(Continued)

OTHER PUBLICATIONS

Chinese Examination Report; dated Feb. 24, 2016; 5 pages.
(Continued)

*Primary Examiner* — Steven O Douglas
(74) *Attorney, Agent, or Firm* — Knobbe Martens Olson and Bear LLP

(57) ABSTRACT

A respiratory assistance apparatus has a gases inlet configured to receive a supply of gases, a blower unit configured to generate a pressurized gases stream from the supply of gases; a humidification unit configured to heat and humidify the pressurized gases stream; and a gases outlet for the heated and humidified gases stream. A flow path for the gases stream extends through the respiratory device from the gases inlet through the blower unit and humidification unit to the gases outlet. A sensor assembly is provided in the flow path before the humidification unit. The sensor assembly has
(Continued)

an ultrasound gas composition sensor system for sensing one or more gas concentrations within the gases stream.

21 Claims, 19 Drawing Sheets

(51) Int. Cl.
| | |
|---|---|
| A61M 16/16 | (2006.01) |
| G01N 29/024 | (2006.01) |
| A61M 16/06 | (2006.01) |
| A61M 16/08 | (2006.01) |
| A61M 16/20 | (2006.01) |

(52) U.S. Cl.
CPC .... *A61M 16/0066* (2013.01); *A61M 16/0069* (2014.02); *A61M 16/024* (2017.08); *A61M 16/06* (2013.01); *A61M 16/0875* (2013.01); *A61M 16/101* (2014.02); *A61M 16/1075* (2013.01); *A61M 16/16* (2013.01); *A61M 16/20* (2013.01); *G01N 29/024* (2013.01); *A61M 16/161* (2014.02); *A61M 2016/003* (2013.01); *A61M 2016/0039* (2013.01); *A61M 2016/1025* (2013.01); *A61M 2202/0208* (2013.01); *A61M 2205/12* (2013.01); *A61M 2205/18* (2013.01); *A61M 2205/3334* (2013.01); *A61M 2205/3365* (2013.01); *A61M 2205/3368* (2013.01); *A61M 2205/3375* (2013.01); *A61M 2205/52* (2013.01); *A61M 2205/581* (2013.01); *A61M 2205/582* (2013.01); *A61M 2205/583* (2013.01); *G01N 2291/0212* (2013.01); *G01N 2291/0215* (2013.01); *G01N 2291/048* (2013.01)

(58) Field of Classification Search
CPC ............... A61M 16/06; A61M 16/101; A61M 16/0066; A61M 16/16; A61M 16/1075; A61M 2205/18; A61M 2205/3334; A61M 2205/52; G01N 29/024; G01N 2291/0212; G01N 2291/0215; G01N 2291/048

See application file for complete search history.

(56) References Cited

U.S. PATENT DOCUMENTS

| | | | |
|---|---|---|---|
| 2,283,750 A | 5/1942 | Mikelson | |
| 2,568,277 A | 9/1951 | Eltgroth | |
| 2,874,564 A | 2/1959 | Martin et al. | |
| 2,984,097 A | 5/1961 | Kniazuk et al. | |
| 3,120,750 A | 2/1964 | Root, III | |
| 3,343,403 A | 9/1967 | Romani et al. | |
| 3,468,157 A | 9/1969 | Burk et al. | |
| 3,724,484 A | 4/1973 | Turman | |
| 3,762,197 A | 10/1973 | Roof et al. | |
| 3,805,590 A | 4/1974 | Ringwall et al. | |
| 3,848,457 A | 11/1974 | Behymer | |
| 3,863,630 A | 2/1975 | Cavallo | |
| 3,981,176 A | 9/1976 | Jacobs | |
| 4,155,246 A | 5/1979 | Dempster et al. | |
| 4,215,409 A | 7/1980 | Strowe | |
| 4,220,040 A | 9/1980 | Noguchi et al. | |
| 4,255,964 A | 3/1981 | Morison | |
| 4,280,183 A | 7/1981 | Santi | |
| 4,313,436 A | 2/1982 | Schwanbom et al. | |
| 4,326,513 A | 4/1982 | Schulz et al. | |
| 4,331,025 A * | 5/1982 | Ord, Jr. ............ | G01F 1/66 73/54.01 |
| 4,340,044 A | 7/1982 | Levy et al. | |
| 4,345,612 A | 8/1982 | Koni et al. | |
| 4,380,167 A | 4/1983 | Longini | |
| 4,452,090 A | 6/1984 | Kou et al. | |
| 4,520,654 A | 6/1985 | Terhune | |
| 4,555,932 A | 12/1985 | Crosby, Jr. | |
| 4,662,212 A | 5/1987 | Noguchi et al. | |
| 4,773,448 A | 9/1988 | Francis | |
| 4,938,066 A | 7/1990 | Dorr | |
| 4,989,595 A | 2/1991 | De Vuono et al. | |
| 5,060,506 A | 10/1991 | Douglas | |
| 5,060,507 A | 10/1991 | Urmson et al. | |
| 5,060,514 A * | 10/1991 | Aylsworth ........... | G01N 29/024 73/24.01 |
| 5,179,862 A | 1/1993 | Lynnworth | |
| 5,247,826 A | 9/1993 | Frola et al. | |
| 5,285,677 A | 2/1994 | Oehler | |
| 5,313,820 A | 5/1994 | Aylsworth | |
| 5,343,760 A | 9/1994 | Sultan et al. | |
| 5,351,522 A | 10/1994 | Lura | |
| 5,359,897 A | 11/1994 | Hamstead et al. | |
| 5,392,635 A | 2/1995 | Cadet et al. | |
| 5,452,621 A | 9/1995 | Aylsworth et al. | |
| 5,452,714 A | 9/1995 | Anderson et al. | |
| 5,460,175 A | 10/1995 | Foote et al. | |
| 5,463,906 A | 11/1995 | Spani et al. | |
| 5,581,014 A | 12/1996 | Douglas | |
| 5,625,140 A | 4/1997 | Cadet et al. | |
| 5,627,323 A | 5/1997 | Stern | |
| 5,701,883 A | 12/1997 | Hete et al. | |
| 5,792,665 A | 8/1998 | Morrow, III | |
| 5,823,186 A | 10/1998 | Rossen et al. | |
| 5,917,135 A | 6/1999 | Michaels et al. | |
| 6,039,696 A | 3/2000 | Bell | |
| 6,123,074 A | 9/2000 | Hete et al. | |
| 6,138,674 A | 10/2000 | Gull et al. | |
| 6,142,149 A | 11/2000 | Steen | |
| 6,279,379 B1 | 8/2001 | Logue et al. | |
| 6,397,841 B1 | 6/2002 | Kenyon et al. | |
| 6,487,916 B1 * | 12/2002 | Gomm ............... | G01F 1/667 73/861.27 |
| 6,543,449 B1 | 4/2003 | Woodring et al. | |
| 6,634,356 B1 | 10/2003 | O'Dea et al. | |
| 7,063,668 B2 | 6/2006 | Cardelius et al. | |
| 7,066,175 B2 | 6/2006 | Hamilton et al. | |
| 7,111,624 B2 | 9/2006 | Thudor et al. | |
| 7,370,651 B2 | 5/2008 | Holder | |
| 7,448,376 B2 | 11/2008 | Lepel | |
| 7,509,957 B2 | 3/2009 | Duquette et al. | |
| 8,042,535 B2 * | 10/2011 | Kenyon ................ | A61M 16/00 122/4 R |
| 8,047,082 B2 * | 11/2011 | Bierl ........................ | G01F 1/66 73/861.04 |
| 8,561,611 B2 | 10/2013 | Shissler et al. | |
| 8,746,037 B2 * | 6/2014 | Matsuzaki ........... | G01N 29/024 73/24.01 |
| 8,875,587 B2 | 11/2014 | Wiest et al. | |
| 9,302,066 B2 | 4/2016 | Bertinetti et al. | |
| 9,649,459 B2 | 5/2017 | Taylor et al. | |
| 2002/0062681 A1 | 5/2002 | Livingston | |
| 2004/0211244 A1 | 10/2004 | Cardelius et al. | |
| 2005/0121033 A1 | 6/2005 | Starr et al. | |
| 2006/0042638 A1 | 3/2006 | Niklewski et al. | |
| 2006/0283450 A1 | 12/2006 | Shissler et al. | |
| 2007/0044799 A1 | 3/2007 | Hete et al. | |
| 2007/0125374 A1 | 6/2007 | Smith et al. | |
| 2007/0283958 A1 | 12/2007 | Naghavi | |
| 2008/0041381 A1 | 2/2008 | Tham et al. | |
| 2008/0156328 A1 | 7/2008 | Taube | |
| 2009/0020120 A1 | 1/2009 | Schatzl et al. | |
| 2009/0056715 A1 | 3/2009 | Cortez, Jr. et al. | |
| 2009/0107501 A1 | 4/2009 | Krieger | |
| 2009/0145428 A1 | 6/2009 | Sward et al. | |
| 2009/0178490 A1 * | 7/2009 | Konzelmann ........... | G01F 1/662 73/861.29 |
| 2009/0241953 A1 | 10/2009 | Vandine et al. | |
| 2010/0006098 A1 | 1/2010 | McGinnis et al. | |
| 2010/0218591 A1 | 9/2010 | Rhodes et al. | |
| 2010/0224191 A1 | 9/2010 | Dixon et al. | |
| 2011/0120462 A1 * | 5/2011 | Tatkov ............... | A61M 16/1075 128/203.14 |
| 2012/0055340 A1 | 3/2012 | Wilkinson et al. | |

(56) References Cited

U.S. PATENT DOCUMENTS

| | | |
|---|---|---|
| 2012/0065533 A1 | 3/2012 | Carrilo et al. |
| 2012/0125121 A1 | 5/2012 | Gottlieb et al. |
| 2013/0239960 A1 | 9/2013 | Bertinetti et al. |
| 2014/0034051 A1 | 2/2014 | Addington et al. |
| 2015/0059745 A1 | 3/2015 | Barker et al. |
| 2015/0107587 A1 | 4/2015 | Zhang |
| 2016/0082220 A1 | 3/2016 | Barker et al. |
| 2017/0197056 A1 | 7/2017 | Van Schalkwyk et al. |

FOREIGN PATENT DOCUMENTS

| | | |
|---|---|---|
| DE | 404809 | 10/1924 |
| EP | 813060 | 12/1997 |
| EP | 1083427 B1 | 3/2001 |
| EP | 1138341 | 10/2001 |
| EP | 1205747 | 5/2002 |
| EP | 1286159 A1 | 2/2003 |
| EP | 1961439 | 8/2008 |
| EP | 2200687 | 6/2010 |
| GB | 2087559 | 5/1982 |
| JP | 55-004528 | 1/1980 |
| JP | S58-190439 | 12/1983 |
| JP | H01-321508 | 12/1989 |
| JP | 10-073574 | 3/1998 |
| JP | 2001-120661 | 5/2001 |
| JP | 2011-120661 | 5/2001 |
| JP | 2002-214012 | 7/2002 |
| JP | 2002306603 | 10/2002 |
| JP | 2005-537083 | 12/2005 |
| JP | 2008-518640 | 6/2008 |
| JP | 2010-537779 | 12/2010 |
| JP | 2011-521705 | 7/2011 |
| WO | WO 95/28193 | 10/1995 |
| WO | WO 2000/045883 | 8/2000 |
| WO | WO 03/090903 | 11/2003 |
| WO | WO 2004/039444 | 5/2004 |
| WO | WO 2004/069922 | 8/2004 |
| WO | WO 2004/112873 | 12/2004 |
| WO | WO 2007/004898 | 1/2007 |
| WO | WO 2007/069922 | 6/2007 |
| WO | WO 2008/149868 | 5/2008 |
| WO | WO 2009/045198 | 4/2009 |
| WO | WO 2009/052631 | 4/2009 |
| WO | WO 2009/058081 | 5/2009 |
| WO | WO 2011/010191 | 1/2011 |
| WO | WO 2011/057196 | 5/2011 |
| WO | WO 2011/058196 | 5/2011 |
| WO | WO 2011/058196 A1 | 5/2011 |
| WO | WO 2011/075030 | 6/2011 |
| WO | WO 2012/021557 | 2/2012 |
| WO | WO 2013/128365 | 9/2013 |
| WO | WO 2013/151447 | 10/2013 |
| WO | WO 2014/059405 | 4/2014 |
| WO | WO 2015/038013 | 3/2015 |
| WO | WO 2015/183107 | 12/2015 |
| WO | WO 2015/183107 A1 | 12/2015 |
| WO | WO 2017/095241 | 6/2017 |

OTHER PUBLICATIONS

European Search Report; dated Oct. 13, 2015; 7 pages.
Written Opinion of the International Search Authority; PCT/NZ2013/000059; dated Jun. 30, 2013; 4 pages.
Japanese Office Action; dated Mar. 1, 2017; 4 pages.
Australian Examination Report; dated Mar. 28, 2017; 4 pages.
International Preliminary Report on Patentability in International Patent Application No. PCT/NZ2015/050068, dated Dec. 8, 2016, in 9 pages.
International Search Report in International Patent Application No. PCT/NZ2015/050068, dated Oct. 29, 2015, in 7 pages.
International Preliminary Report on Patentability in International Patent Application No. PCT/NZ2015/050068, dated Nov. 29, 2016, in 8 pages.
International Search Report and Written Opinion for PCT/NZ2016/050193 dated Jun. 7, 2017 in 29 pages.
International Search Report; PCT/NZ2013/000059; dated Jun. 30, 2013; 5 pages.
European Search Report for Appl. No. 18200021.6 dated Jan. 25, 2019 in 6 pages.
United Kingdom Search and Examination Report for Application No. GB1816023.4, dated Jan. 28, 2019.
United Kingdom Search and Examination Report for Application No. GB1821238.1, dated Jan. 28, 2019.
Canadian Examination Report for Application No. 2,869,471, dated Feb. 6, 2019.
Japanese Office Action for Application No. 2018-042545, 4 pages.
Australian Examination Report for Application No. 2018204819, dated Mar. 21, 2019.
United Kingdom Search and Examination Report for Application No. GB1821238.1, dated May 2, 2019.
United Kingdom Search and Examination Report for Application No. GB1902906.5, dated Apr. 12, 2019.

* cited by examiner

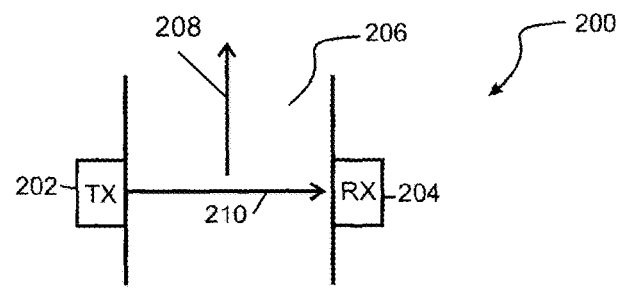
FIGURE 26A
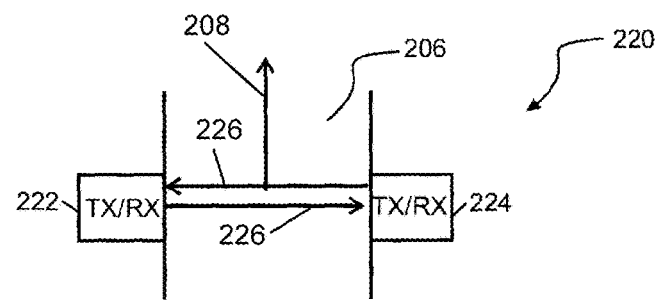
FIGURE 26B
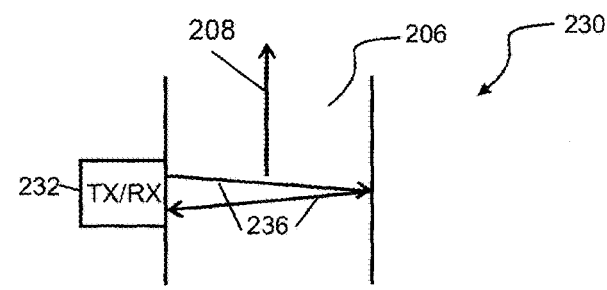
FIGURE 26C
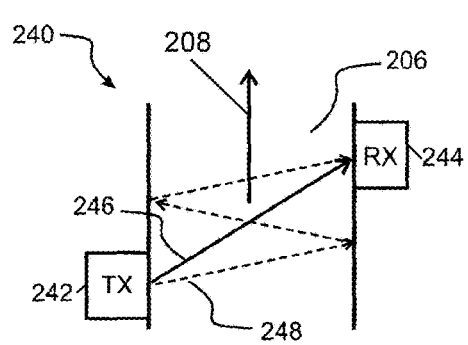
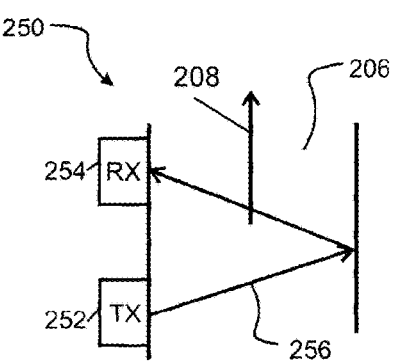
FIGURE 26D  FIGURE 26E

RESPIRATORY ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention relates to respiratory assistance apparatus that provides a stream of heated and humidified gases to a user for therapeutic purposes. In particular, although not exclusively, the respiratory assistance apparatus may provide respiratory assistance to patients or users who require a supply of heated and humidified gases for respiratory therapies such as respiratory humidification therapy, high-flow oxygen therapy, Positive Airway Pressure (PAP) therapies, including CPAP therapy, Bi-PAP therapy, and OPAP therapy, and typically for the treatment of diseases such as Obstructive Sleep Apnea (OSA), snoring, or Chronic Obstructive Pulmonary Disease (COPD).

Description of the Related Art

Respiratory assistance devices or systems for providing a flow of humidified and heated gases to a patient for therapeutic purposes are well known in the art. Systems for providing therapy of this type (for example respiratory humidification) typically have a structure where gases are delivered to a humidifier chamber from a gases source, such as a blower (also known as a compressor, an assisted breathing unit, a fan unit, a flow generator or a pressure generator). As the gases pass over the hot water, or through the heated and humidified air in the humidifier chamber, they become saturated with water vapour. The heated and humidified gases are then delivered to a user or patient downstream from the humidifier chamber, via a gases conduit and a user interface.

In one form, such respiratory assistance systems can be modular systems that comprise a humidifier unit and a blower unit that are separate (modular) items. The modules are connected in series via connection conduits to allow gases to pass from the blower unit to the humidifier unit. For example, FIG. 1 shows a schematic view of a user 1 receiving a stream of heated and humidified air from a modular respiratory assistance system. Pressurised air is provided from an assisted breathing unit or blower unit 2a via a connector conduit 10 to a humidifier chamber 4a. The stream of humidified, heated and pressurised air exits the humidification chamber 4a via a user conduit 3, and is provided to the patient or user 1 via a user interface 5.

In an alternative form, the respiratory assistance systems can be integrated systems in which the blower unit and the humidifier unit are contained within the same housing. A typical integrated system consists of a main blower unit or assisted breathing unit which provides a pressurised gases flow, and a humidifier unit that mates with or is otherwise rigidly connected to the blower unit. For example, the humidifier unit is mated to the blower unit by slide-on or push connection, which ensures that the humidifier unit is rigidly connected to and held firmly in place on the main blower unit. FIG. 2 shows a schematic view of the user 1 receiving heated and humidified air from an integrated respiratory assistance system 6. The system operates in the same manner as the modular system shown in FIG. 1, except the humidification chamber 4b has been integrated with the blower unit to form the integrated system 6.

The user interface 5 shown in FIGS. 1 and 2 is a nasal mask, covering the nose of the user 1. However, it should be noted that in systems of these types, a mask that covers the mouth and nose, a full face mask, a nasal cannula, or any other suitable user interface could be substituted for the nasal mask shown. A mouth-only interface or oral mask could also be used. Also, the patient or user end of the conduit can be connected to a tracheostomy fitting, or an endotracheal intubation.

U.S. Pat. No. 7,111,624 includes a detailed description of an integrated system. A 'slide-on' water chamber is connected to a blower unit in use. A variation of this design is a slide-on or clip-on design where the chamber is enclosed inside a portion of the integrated unit in use. An example of this type of design is shown in WO 2004/112873, which describes a blower, or flow generator 50, and an associated humidifier 150.

For these integrated systems, the most common mode of operation is as follows: air is drawn by the blower through an inlet into the casing which surrounds and encloses at least the blower portion of the system. The blower pressurises the air stream from the flow generator outlet and passes this into the humidifier chamber. The air stream is heated and humidified in the humidifier chamber, and exits the humidifier chamber via an outlet. A flexible hose or conduit is connected either directly or indirectly to the humidifier outlet, and the heated, humidified gases are passed to a user via the conduit. This is shown schematically in FIG. 2.

In both modular and integrated systems, the gases provided by the blower unit are generally sourced from the surrounding atmosphere. However, some forms of these systems may be configured to allow a supplementary gas to be blended with the atmospheric air for particular therapies. In such systems, a gases conduit supplying the supplemental gas is typically either connected directly to the humidifier chamber or elsewhere on the high pressure (flow outlet) side of the blower unit, or alternatively to the inlet side of the blower unit as described in WO 2007/004898. This type of respiratory assistance system is generally used where a patient or user requires oxygen therapy, with the oxygen being supplied from a central gases source. The oxygen from the gases source is blended with the atmospheric air to increase the oxygen fraction before delivery to the patient. Such systems enable oxygen therapy to be combined with high flow humidification therapy for the treatment of diseases such as COPD. In such therapies, it is important that the oxygen fraction being delivered to the patient be known and controlled. Currently, the oxygen fraction being delivered to the patient is typically manually calculated or estimated based on a printed look-up table that sets out various oxygen fractions that have been pre-calculated based on a range of oxygen flow rates supplied from the central gas source and a range of flow rates generated by the blower unit.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide a respiratory assistance apparatus with an improved gas composition sensing capability, or to at least provide the public with a useful choice.

SUMMARY OF THE INVENTION

In a first aspect, the present invention broadly consists in a respiratory assistance apparatus configured to provide a heated and humidified gases stream, comprising: a gases inlet configured to receive a supply of gases; a blower unit configured to generate a pressurised gases stream from the supply of gases; a humidification unit configured to heat and humidify the pressurised gases stream; a gases outlet for the heated and humidified gases stream; a flow path for the gases stream through the respiratory device from the gases inlet through the blower unit and humidification unit to the gases outlet; a sensor assembly provided in the flow path before the humidification unit, the sensor assembly comprising an ultrasound gas composition sensor system for sensing one or more gas concentrations within the gases stream.

Preferably, the ultrasound gas composition sensor system may comprise a transmitter and receiver transducer pair that may be operable to transmit cross-flow acoustic pulses from the transmitter to the receiver through the gases stream for sensing the speed of sound in the gases stream in the vicinity of the sensor assembly.

In one form, the transmitter and receiver transducer pair may be arranged such that the acoustic pulses traverse the gases stream in a cross-flow that is in a direction substantially perpendicular to the flow direction of the gases stream.

In another form, the transmitter and receiver transducer pair may be arranged such that the acoustic pulses traverse the gases stream in a cross-flow that is angled but not perpendicular with respect to the flow direction of the gases stream.

In one form, the transmitter and receiver transducer pair may comprise a transducer that is configured as a transmitter and a transducer that is configured as a receiver for transmitting uni-directional acoustic pulses.

In another form, the transmitter and receiver transducer pair may comprise a pair of transmitter-receiver transducers that are configured for transmitting bi-directional acoustic pulses.

In one form, the transmitter and receiver may be aligned with each other in relation to the flow direction of the gases stream and facing each other on opposite sides of the flow path.

In another form, the transmitter and receiver may be displaced from each other in the flow direction of the gases stream.

Preferably, the acoustic pulses may have a beam path that is direct between the transmitter and receiver. Alternatively, the acoustic pulses may have a beam path that is indirect between the transmitter and receiver and which undergoes one or more reflections.

In another form, the transmitter and receiver transducer pair may be in the form of a single transmitter-receiver that is configured to transmit cross-flow acoustic pulses and receive the echo return pulses.

In another form, the ultrasound gas composition sensor system may comprise a transmitter and receiver transducer pair that are operable to transmit along-flow acoustic pulses from the transmitter to the receiver through the gases stream for sensing the speed of sound in the gases stream in the vicinity of the sensor assembly.

Preferably, the respiratory assistance apparatus may further comprise a sensor control system that is operatively connected to the transmitter and receiver transducer pair of the ultrasound gas composition sensor system and which is configured to operate the transducer pair to sense and generate a speed of sound signal indicative of the speed of sound through the gases stream.

Preferably, the sensor control system is configured to generate one or more gas concentration signals indicative of the gas concentration within the gases stream based at least on the signal indicative of the speed of sound though the gases stream.

In one form, the sensor assembly may further comprise a temperature sensor that is configured to measure the temperature of the gases stream in the vicinity of the sensor assembly and generate a representative temperature signal, and wherein the sensor control system is configured to generate one or more gas concentration signals indicative of the gas concentration within the gases stream based on the speed of sound signal, and the temperature signal.

In another form, the sensor assembly may further comprise a humidity sensor that is configured to measure the humidity of the gases stream in the vicinity of the sensor assembly and generate a representative humidity signal, and wherein the sensor control system is configured to generate one or more gas concentration signals indicative of the gas concentration within the gases stream based on the speed of sound signal, and the humidity signal. By way of example, the humidity sensor may be a relative humidity sensor or an absolute humidity sensor.

In another form, the sensor assembly may comprise both a temperature sensor and a humidity sensor for measuring the temperature and humidity of the gases stream in the vicinity of the sensor assembly and generating respective representative temperature and humidity signals, and wherein the sensor control system is configured to generate one or more gas concentration signals indicative of the gas concentration within the gases stream based on the speed of sound signal, temperature signal, and humidity signal.

Preferably, the sensor control system may be configured to apply a temperature correction to the temperature signal to compensate for any predicted temperature sensing error created by heat within the respiratory device that affects the temperature sensor.

Preferably, the sensor assembly may further comprise a flow rate sensor that is configured to sense the flow rate of the gases stream in the vicinity of the sensor assembly and generate a representative flow rate signal; and the system may further comprise: a motor speed sensor being provided that is configured to sense the motor speed of the blower unit and generate a representative motor speed signal, and wherein the temperature correction is calculated by the sensor control system based at least on the flow rate signal and/or motor speed signal.

In one form, the sensor control system may be configured to generate a gas concentration signal representing the oxygen concentration in the gases stream.

In another form, the sensor control system may be configured to generate a gas concentration signal representing the carbon dioxide concentration in the gases stream.

Preferably, the sensor assembly may be releasably mounted within the flow path.

Preferably, the flow path may be shaped or configured to promote stable flow of the gases stream in at least one section or portion of the flow path.

Preferably, the flow path may be shaped or configured to promote stable flow in a section or portion of the flow path containing the sensor assembly.

Preferably, the flow path may comprise one or more flow directors at or toward the gases inlet. More preferably, each flow director may be in the form of an arcuate fin.

In one form, the flow path may comprise at least one spiral portion or section to promote stable flow of the gases stream. Preferably, the flow path may comprise an inlet section that extends between the gases inlet and the blower unit and the inlet section comprises at least one spiral portion.

Preferably, the sensor assembly may be located in a spiral portion of the flow path. More preferably, the spiral portion comprises one or more substantially straight sections, and the sensor assembly is located in one of the straight sections.

Preferably, the sensor assembly may comprise a sensor housing comprising a main body that is hollow and defined by peripheral walls that extend between a first open end and a second open end to thereby define a sensing passage in the main body between the walls through which the gases stream may flow in the direction of a flow axis extending between the first and second ends of the main body, and wherein the transmitter and receiver transducer pair are located on opposite walls or sides of the sensing passage. More preferably, the sensor housing may comprise: a main body comprising two spaced-apart side walls, upper and lower walls extending between the side walls to define the sensing passage along the main body between its first and second ends; and a pair of transducer mounting assemblies located on opposing walls of the main body, which are each configured to receive and retain a respective transducer of the transducer pair such that they are aligned, and face each other, across the sensing passage of the main body.

Preferably, the blower unit may be operable to generate a gases stream at the gases outlet having a flow rate of up to 100 liters-per-minute.

In one form, the gases inlet may be configured to receive a supply of gases comprising a mixture of atmospheric air and pure oxygen from an oxygen supply. In another form, the gases inlet may be configured to receive a supply of gases comprising a mixture of atmospheric air and carbon dioxide from a carbon dioxide supply.

Preferably, the flow path is in the bulk flow path of the apparatus.

In a second aspect, the present invention broadly consists in a sensor assembly for in-line flow path sensing of a gases stream in a respiratory assistance apparatus comprising: a sensor housing comprising a main body that is hollow and defined by peripheral walls that extend between a first open end and a second open end, to thereby define a sensing passage in the main body between the walls, through which the gases stream may flow in the direction of a flow axis extending between the first and second ends of the main body; an ultrasound gas composition sensor system mounted in the sensor housing for sensing one or more gas concentrations within the gases stream flowing in the sensing passage; a temperature sensor mounted in the sensor housing for sensing the temperature of the gases stream flowing in the sensing passage; and a flow rate sensor mounted in the sensor housing for sensing the flow rate of the gases stream flowing in the sending passage.

Preferably, the sensor housing may be configured for releasable engagement into a complementary retaining aperture in the flow path of the respiratory assistance apparatus.

Preferably, the ultrasound gas composition sensor system may comprise a transmitter and receiver transducer pair that are operable to transmit acoustic pulses from the transmitter to the receiver through the gases stream in a direction substantially perpendicular to the flow axis of the gases stream flowing through the sensing passage.

Preferably, the transmitter and receiver transducer pair may be located on opposite walls or sides of the sensing passage.

Preferably, the main body of the sensor housing may comprise two spaced-apart side walls, and upper and lower walls that extend between the side walls to define the sensing passage along the main body between its first and second ends; and a pair of transducer mounting assemblies located on opposing walls of the main body, which are each configured to receive and retain a respective transducer of the transducer pair such that they are aligned, and face each other, across the sensing passage of the main body.

Preferably, the pair of transducer mounting assemblies may be located on opposite side walls of the main body, and wherein each transducer mounting assembly comprises a retaining cavity within which a respective transducer of the pair are received and retained.

Preferably, each transducer mounting assembly may comprise a cylindrical base portion that extends from a respective side wall of the main body and at least one pair of opposed clips that extend from the base portion, the base portion and clips collectively defining the retaining cavity.

Preferably, each side wall of the main body may comprise a transducer aperture which is co-aligned with its associated transducer mounting assembly and through which the front operating face of the transducer may extend to access the sensing passage.

Preferably, the transducer mounting assemblies may be configured to locate their respective transducers such that the operating faces of the transducers are substantially flush with the inner surface of their respective wall of the main body of the sensor housing.

The second aspect of the invention may have any one or more of the features mentioned in respect of the sensor assembly of the first aspect of the invention.

The phrase "stable flow" as used in this specification and claims means, unless the context suggests otherwise, a type of gases stream flow, whether laminar or turbulent, that promotes or causes the properties or characteristics of the flow being measured or sensed to be substantially time-invariant for a given set of conditions at the scale the properties or characteristics are being measured or sensed.

The phrases "cross-flow beam" or "cross-flow" as used in this specification and claims mean, unless the context suggests otherwise, an ultrasound pulse or beam that is transmitted in a beam path across or transversely to the main gases flow path direction or axis as opposed to along the main gases flow path direction. For example, a cross-flow beam may be transmitted across the gases flow path in a direction substantially perpendicular to the main gases flow path direction or axis, although other cross-flow angles are intended to be covered by the term also.

The phrases "along-flow beam" or "along-flow" as used in this specification and claims mean, unless the context suggests otherwise, an ultrasound pulse or beam that is transmitted in a beam path that is substantially aligned, whether parallel or coincident, with the main gases flow path direction or axis, whether transmitted in a direction that is with or against the gases flow direction.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

Number Ranges

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIGS. 26A-26E show schematic diagrams of various ultrasonic transducer configurations for the sensor assembly using cross-flow beams.

DETAILED DESCRIPTION OF PREFERRED EMBODIMENTS

Overview

This invention relates primarily to a sensor assembly and associated sensor control circuitry for sensing various characteristics of a stream of gases flowing in a respiratory assistance apparatus. By way of example, an embodiment of the sensor assembly and sensor control system will be described with reference to a respiratory assistance apparatus of the integrated system type in which the blower unit is integrated with the humidification unit in a single housing. However, it will be appreciated that the sensor assembly and associated sensor control system may be implemented in a modular type respiratory assistance apparatus system in which the humidification unit is separate from the blower unit.

Further, the embodiment to be described is with reference to a respiratory assistance apparatus being used particularly for high-flow humidification and oxygen therapy in which the stream of gases can be considered a binary gas mixture of atmospheric air blended with supplementary oxygen (O2) such that the oxygen fraction of the stream of gases delivered to the end user has an increased oxygen fraction relative to atmospheric air. In the art, supplementing or blending the atmospheric gases with another gas is known as 'augmentation' and is typically used to vary the concentration of a particular gas, such as oxygen or nitrogen, relative to its concentration in atmospheric air.

It will be appreciated that the sensor assembly and sensing circuitry may alternatively be implemented in other respiratory assistance apparatuses that are particularly configured for or controlled for use in other respiratory therapies, such as PAP therapies, whether such systems deliver a stream of pressurised gases of atmospheric air only or atmospheric air augmented with another particular gas, such as oxygen or nitrogen. It will be appreciated that while the sensor assembly and sensor control system are primarily configured for sensing the oxygen fraction of a binary gases mixture comprising atmospheric gases augmented with oxygen, the sensor assembly and sensor control system may also be configured or adapted to sense characteristics of a gases stream which comprise other augmented air blends or binary gas mixtures, such as atmospheric air augmented with nitrogen (N2) from a nitrogen supply or augmented with carbon dioxide (CO2) from a carbon dioxide supply or any other suitable supplemental gas, or helium augmented with oxygen or any other suitable binary gas mixtures.

Figure 3:
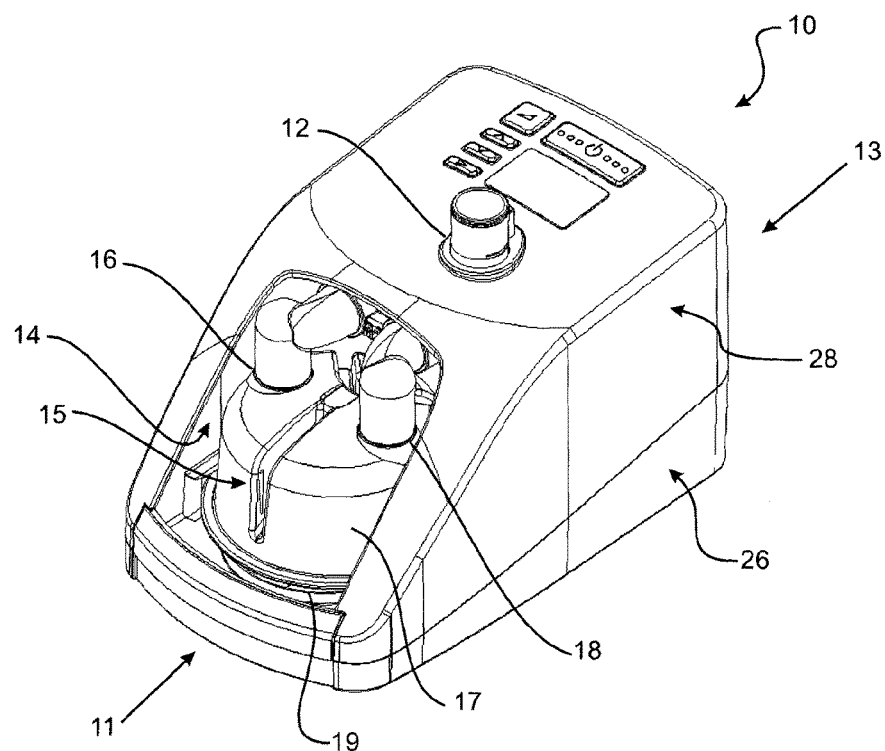
FIG. 3 shows a perspective view of the main housing of a respiratory assistance apparatus in accordance with an embodiment of the invention.
Figure 4:
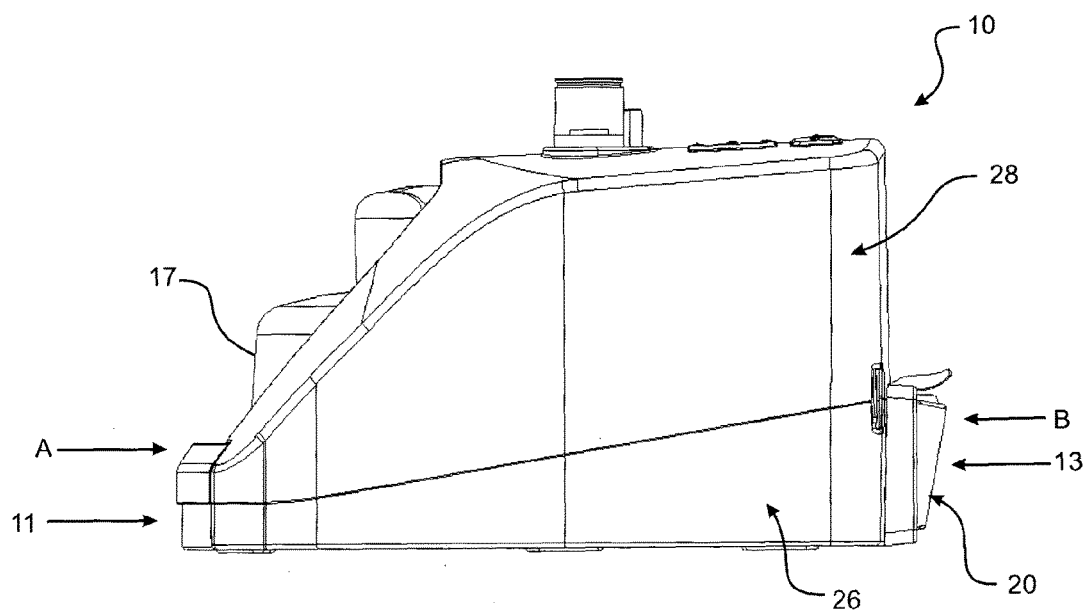
FIG. 4 shows a side elevation view of the respiratory assistance apparatus of FIG. 3.

Integrated Respiratory Assistance Apparatus for High-Flow Humidification and Oxygen Therapy Referring to FIG. 3, the main housing of the integrated respiratory assistance apparatus 10 (respiratory device) in accordance with an embodiment of the invention is shown. The respiratory device 10 comprises a blower unit that generates a stream of pressurised or high-flow gases which is then heated and humidified by a humidification unit in a manner previously described. Although not shown in FIG. 3, the gases stream generated by the respiratory device 10 is typically delivered to a patient by a patient interface that typically comprises a flexible delivery conduit or tube that is connected at one end to a gases outlet 12 of the respiratory device 10, and at the other end, to a user interface, which is typically a nasal cannula, or alternatively may be a nasal mask, full face mask, tracheostomy fitting, or any other suitable user interface.

Figure 1:
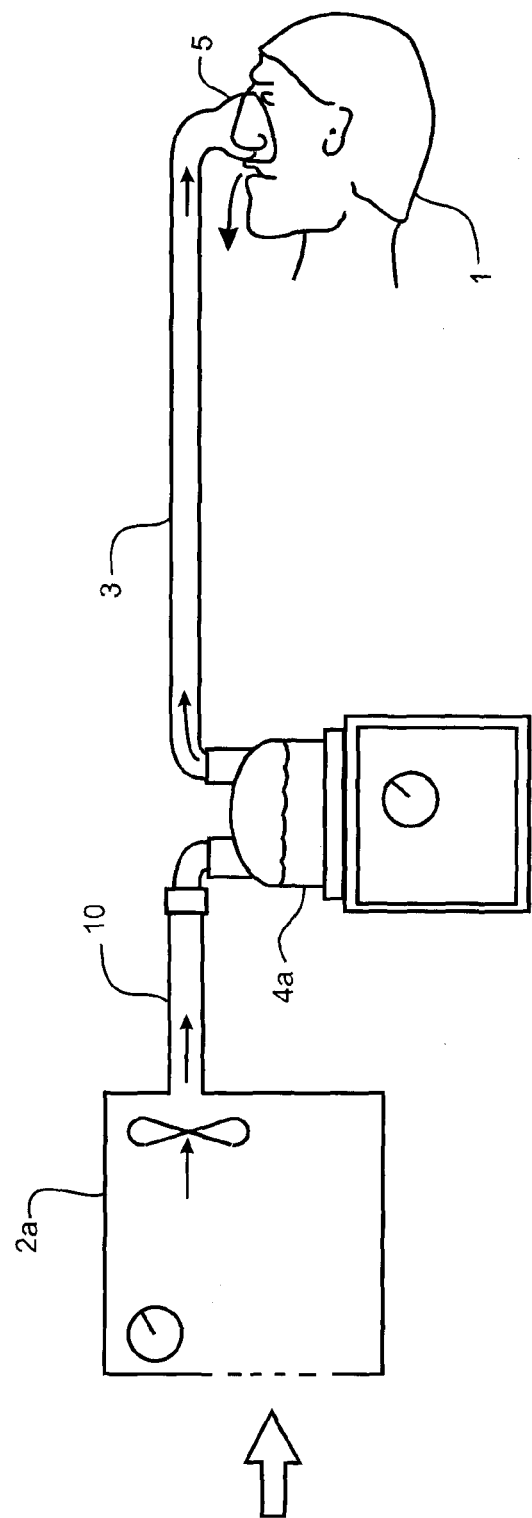
FIG. 1 is a schematic view of a known form of respiratory assistance apparatus having a modular configuration blower unit connected to a humidifier unit.
Figure 2:
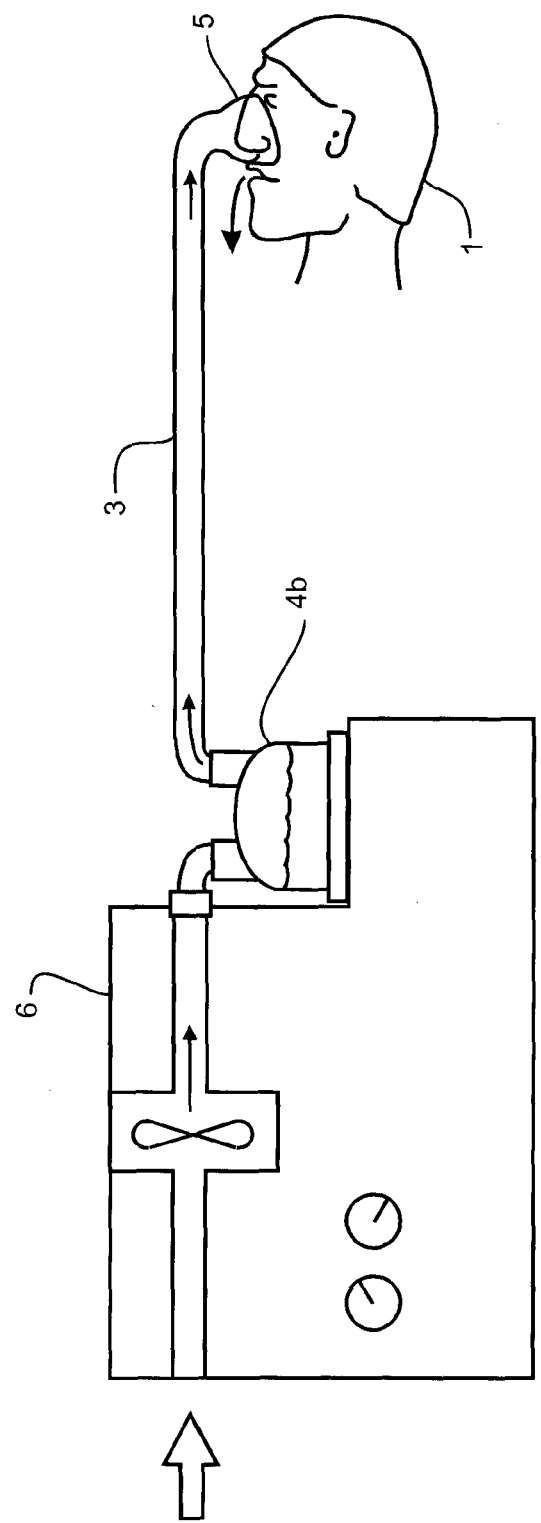
FIG. 2 is a schematic view of another known form of respiratory assistance apparatus in which the blower unit and humidifier unit are integrated into a single main housing.
Figure 5:
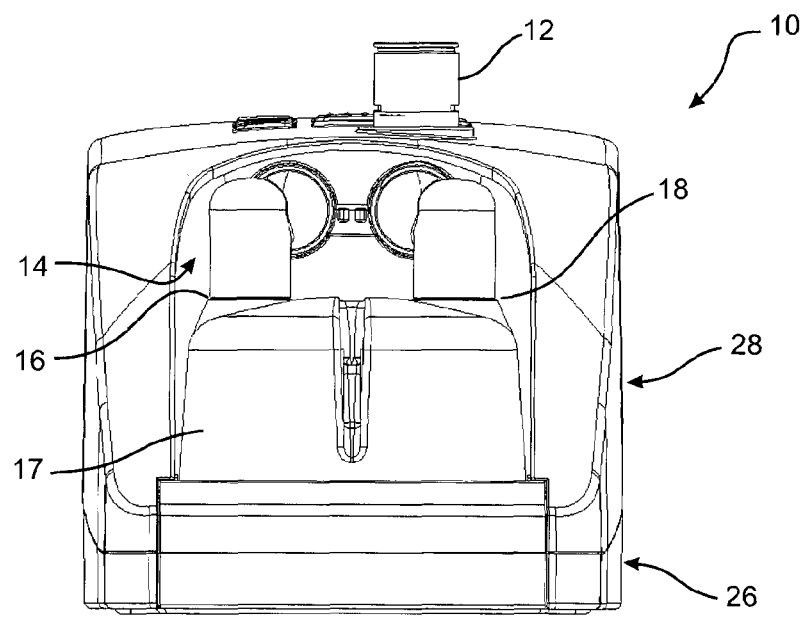
FIG. 5 shows a front elevation view of the respiratory assistance apparatus from direction A in FIG. 4.

In this embodiment, the respiratory device 10 is provided with a humidification unit 15 of the type previously described with reference to FIG. 2 for example. The humidification unit 15 comprises a humidification water chamber 17 and heater plate 19 which are installed within a humidification unit compartment generally indicated at 14 located at or toward the front end 11 of the main housing. Referring to FIGS. 3 and 5, the humidification chamber 17 is provided with an inlet port 16 and outlet port 18 for connecting the chamber into the flow path of the respiratory device when installed. For example, the inlet port 16 is connected into the flow path after the blower unit such that the humidification chamber 17 receives a stream of pressurised or high-flow gases through the inlet from the blower unit located at or toward the rear end 13 of the main housing. Once heated and humidified, the stream of gases exits the humidification chamber via its outlet port 18, which is fluidly connected to the gases outlet 12 of the respiratory device 10.

Figure 6:
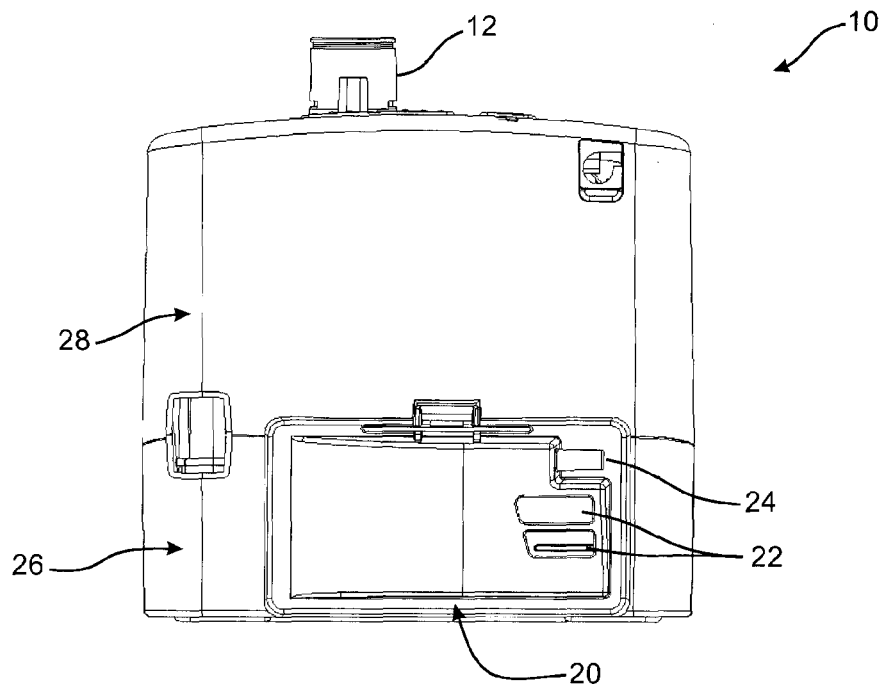
FIG. 6 shows a rear elevation view of the respiratory assistance apparatus from direction B of FIG. 4.

Referring to FIG. 6, a gases inlet assembly 20 of the respiratory device 10 is shown at the rear end 13 of the main housing. In this embodiment, the gases inlet assembly 20 comprises one or more atmospheric air inlet vents 22 through which ambient atmospheric air is drawn into the device by the blower unit and a supplemental gas connection inlet 24 which may be connected to a central gases supply of a supplemental gas, such as a flow of oxygen for blending with the atmospheric air to increase the oxygen fraction. As will be explained in further detail later, the binary gas mixture of air and oxygen is drawn or sucked in by the blower unit and pressurised into a gas stream of a desired flow rate for subsequent delivery into the humidification unit where it is heated and humidified before delivery to the end user via a patient interface to complete the breathing circuit.

Reverting to FIG. 3, in this embodiment the main housing of the respiratory device 10 is of a two-part construction comprising a lower housing part 26 that is releasably coupled or fitted to an upper housing part 28 and which when assembled together form the overall main housing or casing which encloses the blower unit and provides the humidification unit compartment for receiving the humidification chamber. However, it will be appreciated that a multi-part housing construction of more than two parts or a single integral main housing may alternatively be employed. In this embodiment, the housing parts are moulded from plastic, but it will be appreciated that one or more components or parts of the housing may be formed from other materials if desired.

Figure 7:
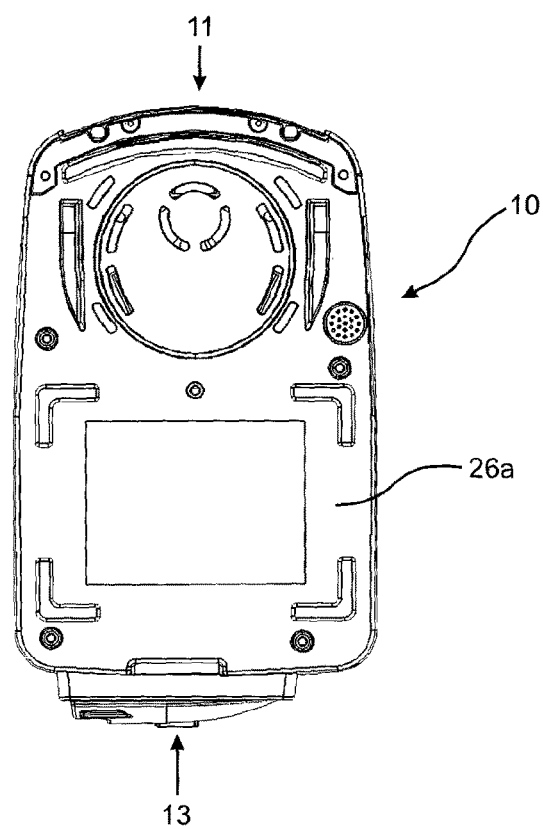
FIG. 7 shows an underside view of the respiratory assistance apparatus of FIG. 3.
Figure 8:
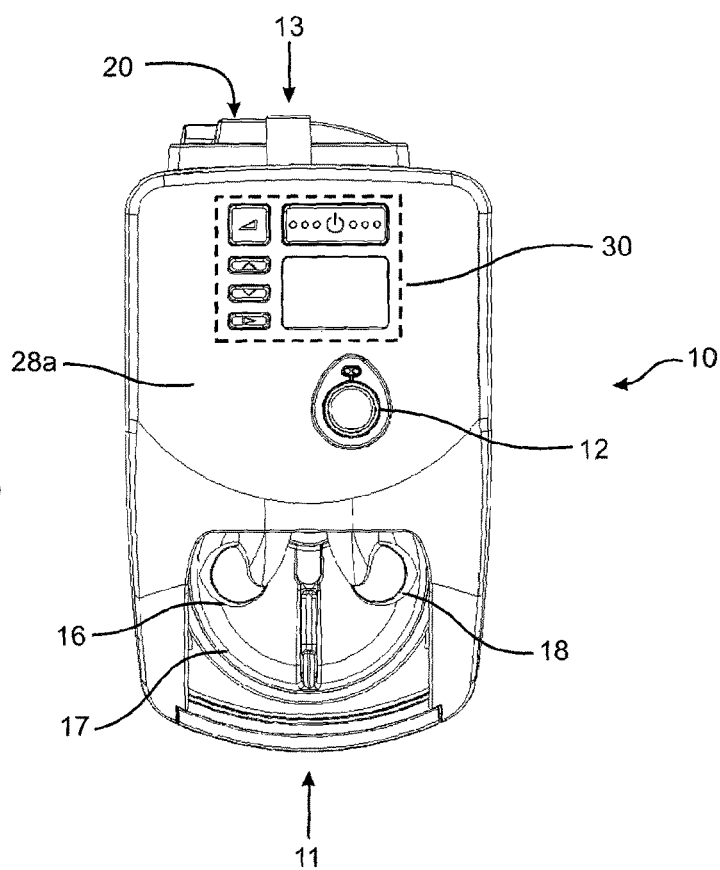
FIG. 8 shows a plan view of the respiratory assistance apparatus of FIG. 3.

Referring to FIG. 7, the main base or underside portion 26a of the lower housing part 26 is shown. Referring to FIG. 8, a user control interface 30 is provided on the main upper portion 28a of the upper housing part 28 and which may comprise user controls and/or a user display for controlling the respiratory device 10.

Figure 9:
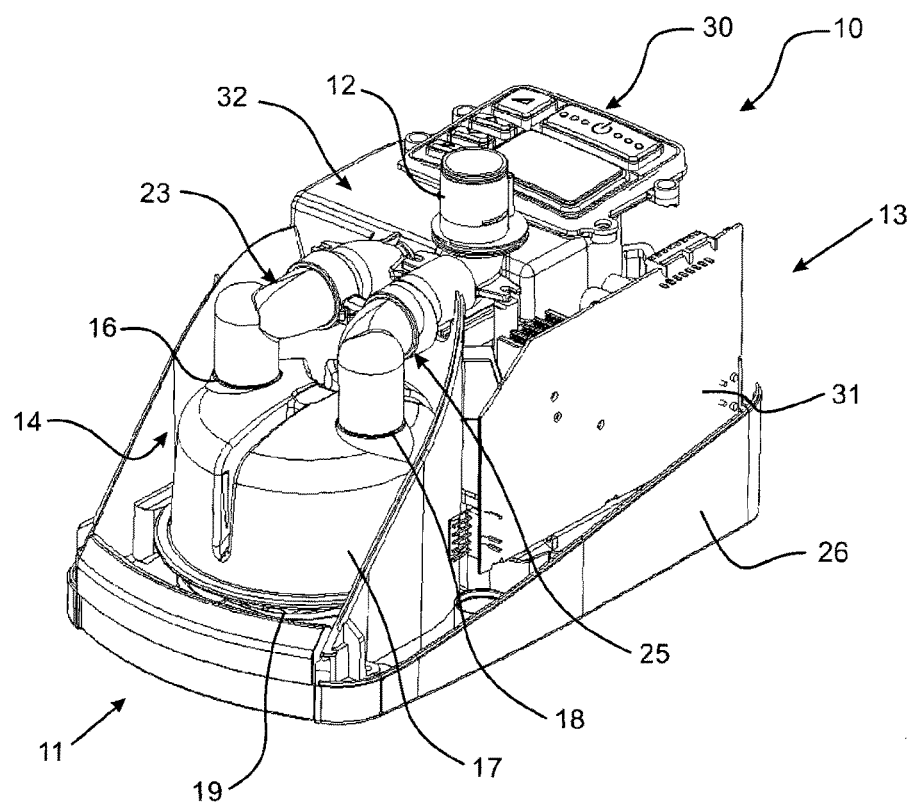
FIG. 9 shows a perspective view of the respiratory assistance apparatus of FIG. 3 with an upper part of the main housing removed and exposing the electronic control circuitry and blower unit compartment.
Figure 10:
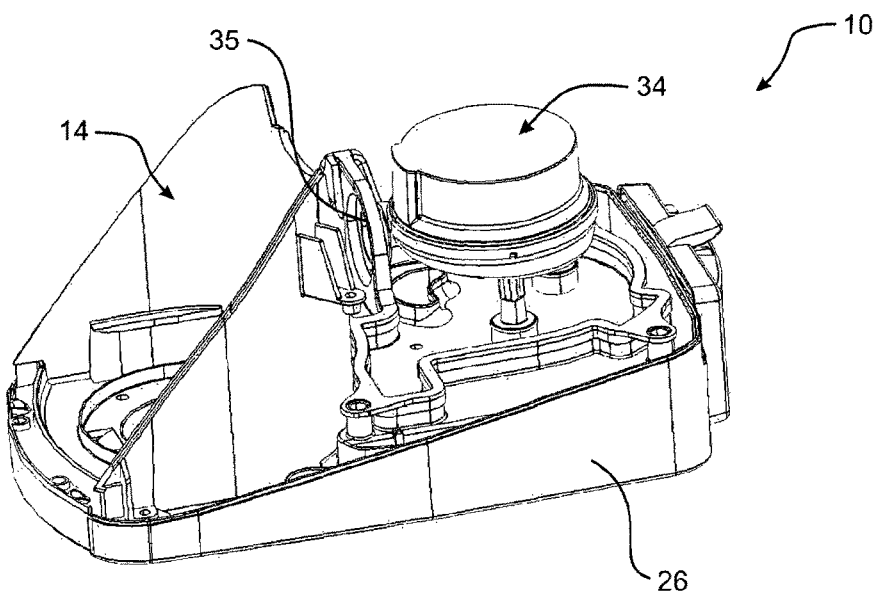
FIG. 10 shows a perspective view of the respiratory assistance apparatus of FIG. 9 with the electronic control circuitry, outer blower unit casing, and other components removed exposing the upper side of the inner blower casing for the motor and impeller.

Referring to FIG. 9, the respiratory device 10 is shown with the upper housing part 28 removed and exposing the main or outer blower unit casing 32 of the blower unit compartment that in this embodiment is housed and located toward the rear end 13 of the main housing. A printed circuit board 31 comprising the control system electronics of the respiratory device 10 and being mounted alongside the blower unit casing 32 is also visible in FIG. 9. Also more clearly shown are the connectors and/or conduits 23,25 which fluidly connect the inlet 16 and outlet 18 ports of the humidification chamber 17 to the blower unit and gases outlet 12, respectively. FIG. 10 shows the inner blower casing 34 which houses the motor and impeller of the blower unit. The gases outlet of the blower unit is indicated generally at 35. The inner blower casing 34 is mounted or housed inside the main blower unit casing 32 shown in FIG. 9.

Figure 10A:
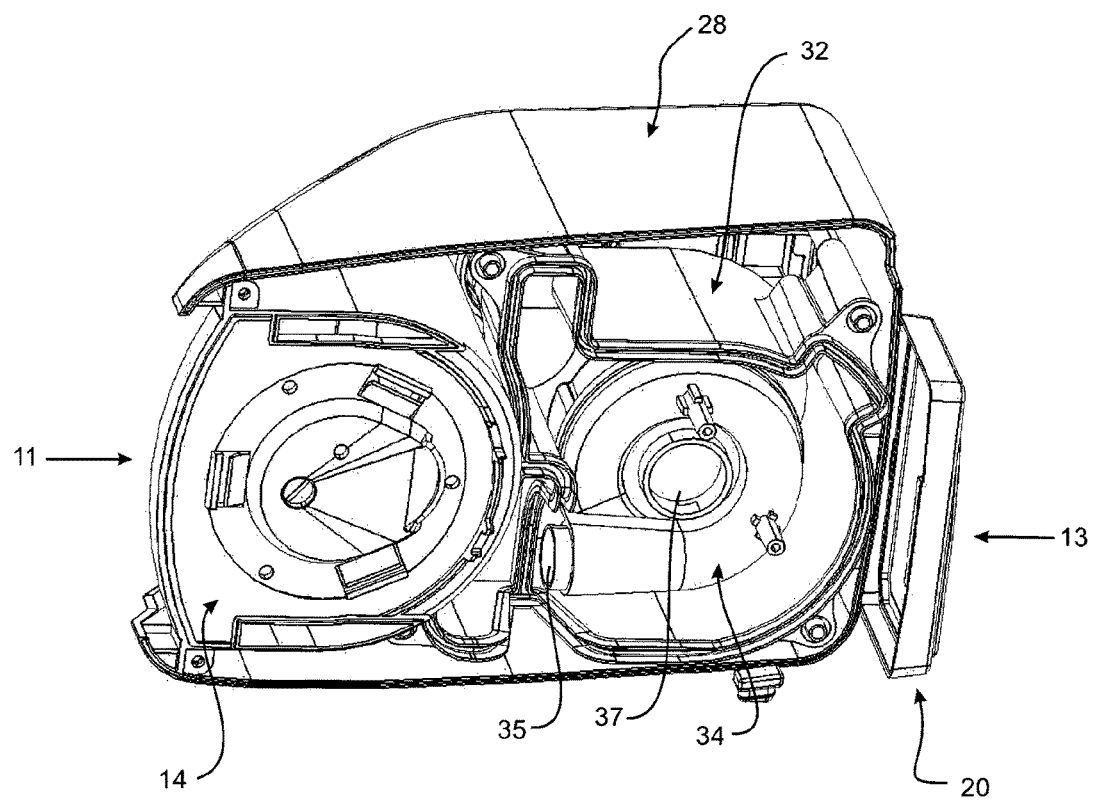
FIG. 10A shows a perspective view of the respiratory assistance apparatus of FIG. 3 with a lower part of the main housing and base compartment removed and exposing the underside of the main outer blower unit casing and inner blower casing.

Referring to FIG. 10A, the gases outlet 35 of the blower unit can be seen more clearly. The blower unit is also provided with a central gases inlet aperture or port 37 through which gases are drawn by the rotating impeller of the blower unit. In this embodiment, the inlet port 37 of the blower unit is fluidly connected by a flow path to the gases inlet assembly 20.

Figure 11:
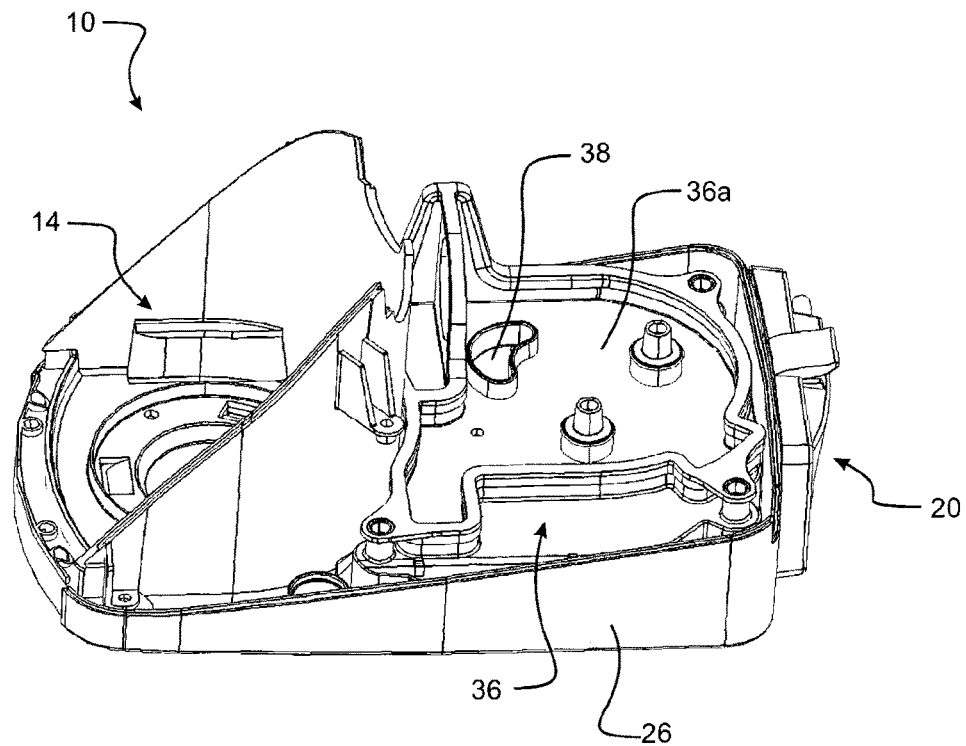
FIG. 11 shows a perspective view of the respiratory assistance apparatus of FIG. 10 with the inner blower casing and humidification chamber inlet connector removed exposing the upper side of the main housing base compartment.
Figure 12:
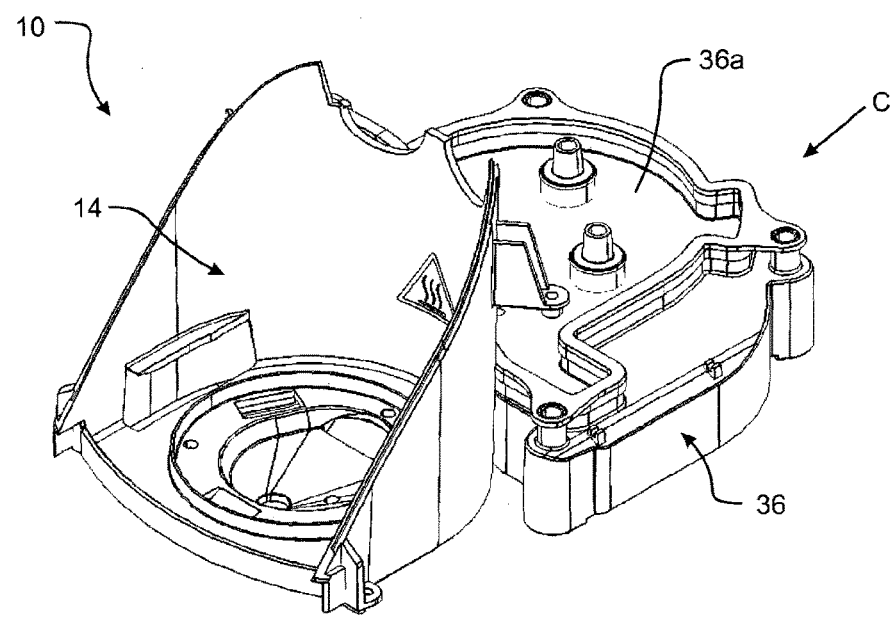
FIG. 12 shows a perspective view of the respiratory assistance apparatus of FIG. 11 with the lower part of the main housing removed exposing the base compartment and humidifier unit compartment.
Figure 13:
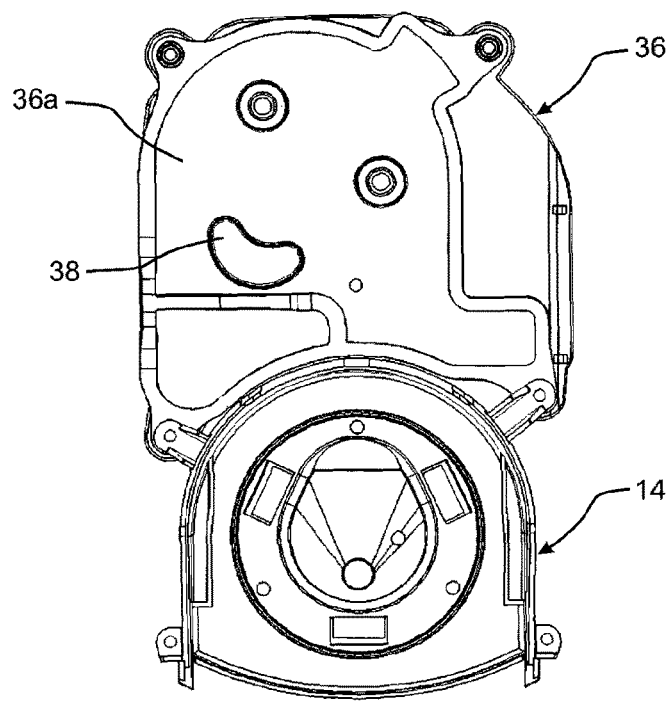
FIG. 13 shows a plan view of the respiratory assistance apparatus of FIG. 12.

Referring to FIG. 11, a base compartment 36 is situated beneath the blower unit at or toward the rear end 13 of the main housing. In this embodiment, the base compartment 36 is mounted to or within the lower housing part 26. The base compartment 36 comprises an exit port or aperture 38 in its upper portion or lid 36a that is fluidly connected by conduit and/or connectors to the inlet port 37 of the blower unit such that in operation the gases stream flows through into the blower unit from the base compartment 36 after entering the gases inlet assembly 20. FIG. 12 shows the base compartment 36 more clearly with the lower housing part 26 of the main housing omitted from view. The humidification unit compartment 14 is also more clearly visible in FIG. 12.

Flow Path of Gases Stream

In operation, the flow or stream of gases is transported from the gases inlet assembly 20 to the gases outlet 12 via a flow path through the respiratory device 10. In this embodiment, the flow path starts at the gases inlet assembly 20 where the stream of gases, such as atmospheric air blended with supplemental oxygen enter the respiratory device 10 and are channeled or transported through an inlet section of the flow path in the base compartment 36 prior to entering the blower unit compartment above. Upon exiting the inlet section of the flow path, the stream of gases enters the blower unit where the gases are pressurised or accelerated into a high flow gas stream having a controllable flow rate, which is typically high flow for high-flow humidification therapies. In such applications, the flow rate may range from about 1 L/min to about 100 L/min, and more preferably from about 2 L/min to about 60 L/min. The flow path exits the blower unit and enters the fluidly connected (e.g. via conduits and/or connectors and/or ports) humidification unit in which the gases stream is heated and humidified. The flow path terminates with the gases stream being transported from the outlet 18 of the humidification unit to the gases outlet 12 of the respiratory device 10.

It will be appreciated that certain portions or sections of the flow path of the gases stream may be fully sealed, for example the flow path after the humidification unit. Additionally, the flow path may also be sealed between the humidification unit and blower unit, and the inlet section of the flow path prior to the blower unit may also optionally be substantially sealed along a significant portion after the gases inlet assembly 20. It will be appreciated that the flow path for transporting the gases stream may be defined by conduits, ports and/or connectors fluidly connecting various components, such as the blower unit to the humidification unit, and/or generally by the formation of the housing and casings within the respiratory device which can be configured with enclosed channels or passages, for example formed from internal walls or surfaces, for directing the gases stream through the respiratory device.

Spiral Inlet Flow Path-First Embodiment

Figure 14:
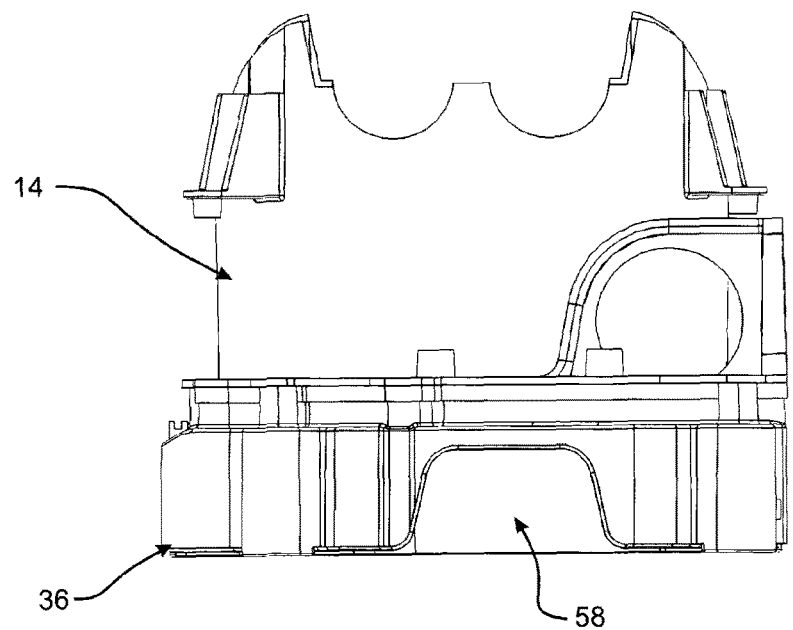
FIG. 14 shows a rear end elevation view of the respiratory assistance apparatus of FIG. 12 from direction C.
Figure 15:
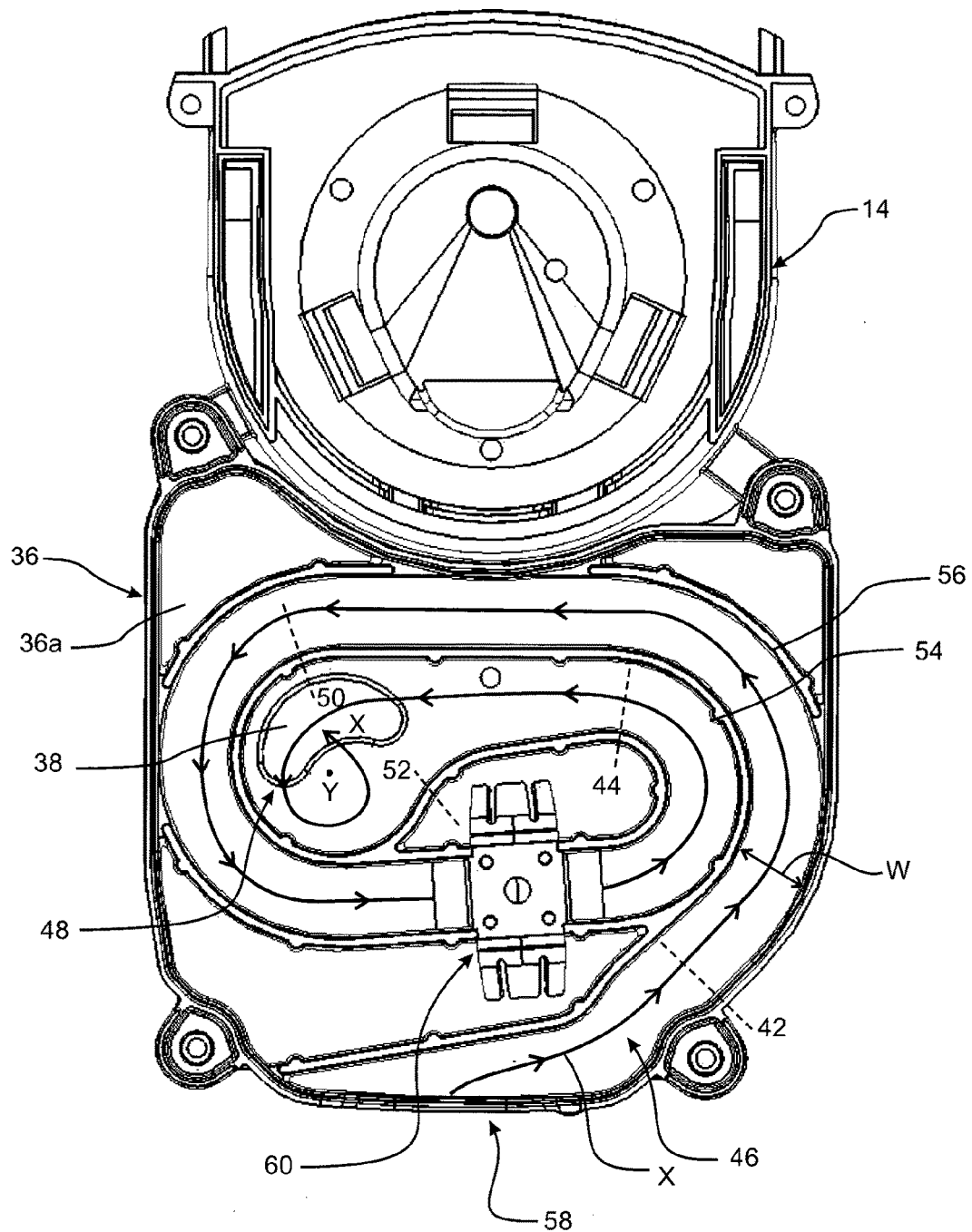
FIG. 15 shows an underside view of the respiratory assistance apparatus of FIG. 12 and showing a sensor assembly and a first embodiment of an inlet section of the gases stream flow path having a spiral flow path.

FIG. 14 shows the inlet aperture 58 formed in the rear of the base compartment 36. The inlet aperture 58 is situated behind gases inlet assembly 20. Referring to FIG. 15, a first embodiment of the inlet section of the gases stream flow path will be described. The inlet section of the gases stream flow path is provided in the base compartment 36 of the main housing and extends from the gases inlet assembly 20 at the rear of the respiratory device 10 to the exit port 38 of the base compartment, prior to entering the inlet port 37 of the blower unit above. As shown in FIG. 15, the inlet section of the flow path as shown generally follows the path shown by arrows XX.

In this embodiment, at least a portion of the inlet section of the flow path is shaped or configured to promote stable air flow upon reaching the exit port 38, and before entering the blower unit compartment via the exit port 38. The stable air flow assists to reduce noise and increases the accuracy of the sensed gas characteristics measured by the sensor assembly in the sensor zone of the flow path. In this embodiment, the stable flow is created or provided by at least a portion of the inlet section of the flow path being spiraled or providing a spiraled course or path. For example, as shown in FIG. 15, at least a portion of the flow path indicated by arrows XX is in the form of a gradually tightening path. The phrases "spiraled" or "spiral" are intended to mean any form of flow path that is continuous and gradually winds in upon itself from a start point to an end point, with one or multiple turns. It is intended to cover any uniform or non-uniform spiral path, whether a continuous and gradually tightening curve of reducing radius relative to a central point or axis wherein the rate of reducing radius may be constant or varied, or an arbitrarily shaped spiral path as shown in FIG. 14 wherein the flow path winds in upon itself (i.e. with at least one turn) such that the path spirals towards a reference point located within the outer most turn, whether the reference point is located centrally or not.

The spiral portion of the flow path may form a substantial part of the entire inlet section of the flow path, or alternatively, may form a minor part of the inlet section of the flow path depending on design requirements. In this embodiment, the spiral portion of the flow path starts at about where indicated at 42 and ends after just over one inward spiral turn at about where indicated at 44. The inlet section of the flow path starts at an inlet zone with an initial section or portion generally indicated at 46 prior to the start 42 of the spiral portion, and then finishes at a terminating section or portion generally indicated at 48 after the end 44 of the spiral portion. In this embodiment, the terminating portion of the inlet section of the flow path is in the form of a gradually widening flow path that opens into a larger transition zone 48 within which the exit port 38 to the blower unit is located. The transition zone 48 comprises a substantially curved perimeter wall that may substantially conform to at least a portion of the circumference of a circle, or which is otherwise curved or concave in shape when viewed in plan. In FIG. 15, the circumferential perimeter wall section of the transition zone is defined between 50 and 52 about centre point Y in the transition zone 48. The shape of the wall in the transition zone is configured to continue to promote stable flow of the gases stream as it exits the inlet section of the flow path and into the blower unit.

As previously described, the flow path within the respiratory device 10 may be formed from a combination of conduit or tubing or the housing or casings of the respiratory device including connectors, ports and/or other couplings that fluidly connect the various sections of the flow path. In this embodiment, the inlet section of the flow path is substantially defined by two co-extending walls 54 and 56 that are spaced-apart from each other and which are enclosed within the base compartment to form an enclosed conduit, channel or passageway by horizontally extending upper and lower walls or surface, such as the upper lid 36a of the base compartment and the base or underside portion 26a of the lower housing part 26 of the main housing (see FIG. 7). As shown in this embodiment, the walls 54, 56 are upright and extend substantially perpendicularly or vertically relative to the substantially horizontal enclosing upper lid 36a of the base compartment and underside portion 26a of the lower housing part 26. It will be appreciated that the flow path defined by the co-extending walls 54 and 56 may alternatively be enclosed from above and/or below by one or more planar plates or members. In this embodiment, the flow path, at least within the spiral portion of the inlet section, has a substantially rectangular or square cross-sectional shape, although it would be appreciated that this is not essential. In alternative embodiments, the flow path may be configured to have any other desired cross-sectional shape, including circular, oval, or otherwise, and the shape may be uniform along the length of the flow path or may vary between two or more shapes and/or sizes. It will also be appreciated that the inlet section and particularly the spiral portion of the inlet section of the flow path may be formed from a rigidly shaped conduit or tubing that is formed to extend in the desired spiral shape.

Figure 17:
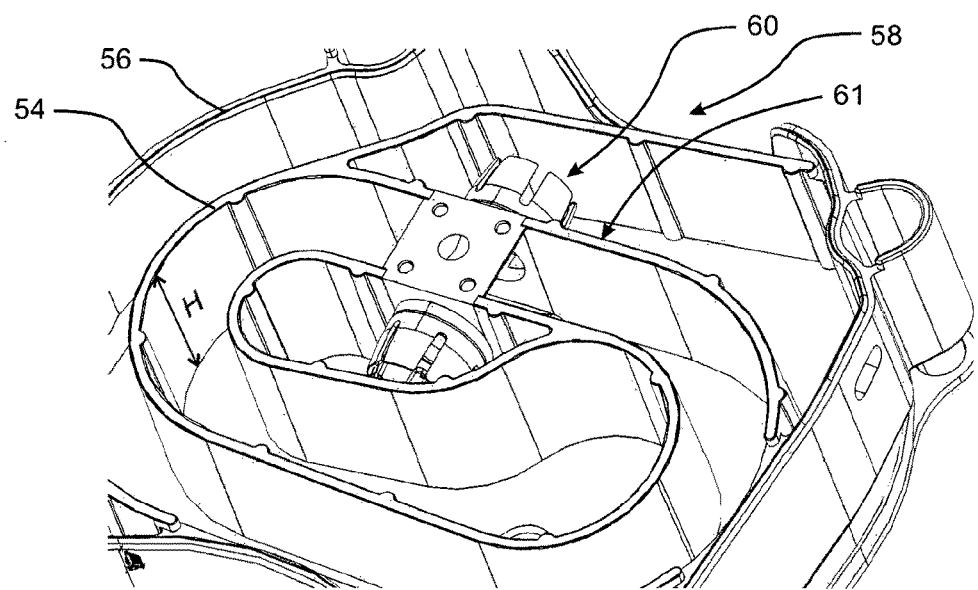
FIG. 17 shows a close-up perspective view of the underside of the respiratory assistance apparatus of FIG. 12 and in particular a portion of the inlet section of the gases stream flow path and sensor assembly.

The cross-sectional area of the spiral portion of the inlet section of the flow path in this embodiment is substantially uniform along the length of the spiral portion, although in alternative embodiments the cross-sectional area may be non-uniform along the length of the spiral portion. In particular, the width (W) between the co-extending walls 54 and 56, is substantially constant throughout the spiral portion of the inlet section in this embodiment, but may be varied along the length of the spiral portion in alternative embodiments if desired. With reference to FIG. 17, the height (H) of the walls is also preferably constant along at least the spiral portion of the inlet section of the flow path, but may be configured to vary in other embodiments if desired.

In this embodiment, the entire inlet section of the flow path extends substantially within the same plane within the base compartment 36 such that there is no vertical deviation or displacement of the flow path within the inlet section, and at least within the spiral portion of the inlet section, until the flow path transitions to the exit port 38 where it extends vertically up into the blower unit casing 32 above the base compartment 36.

In this embodiment, there is a single spiral portion located substantially prior to the transition zone of the flow path where it enters the blower unit compartment 32. However, in alternative embodiments, it will be appreciated that the flow path may comprise two or more separate spiral portions located in series in the flow path. If there are a plurality of spiral portions, they may all be located prior to the blower unit or in the flow path after the blower unit prior to the humidifier unit, or alternatively, at least one spiral portion in each region may be provided. In the preferred embodiment, the spiral portion or portions are provided preferably before the flow path enters the humidification unit, and more preferably, prior to the flow path entering the blower unit, or any other section of the flow path in which stable flow promotion is beneficial for noise reduction or gases stream characteristics sensing accuracy.

Sensor Assembly

Figure 16:
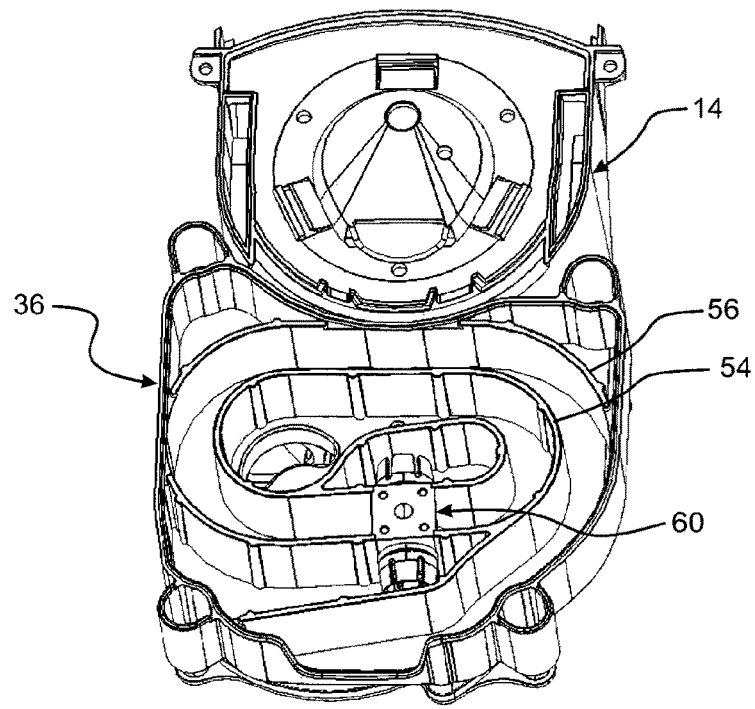
FIG. 16 shows a perspective view of the underside of the respiratory assistance apparatus of FIG. 12.

Referring to FIGS. 15-17, the respiratory device 10 comprises a sensor assembly 60 located or situated in-line with the flow path prior to the humidification unit for sensing various characteristics or parameters of the gases stream. In this embodiment, the sensor assembly 60 is provided in a sensor zone of the inlet section of the flow path, and preferably within the spiral portion of the inlet section of the flow path when the gases stream has stable flow characteristics. The sensor assembly 60 comprises a sensor housing as shown in FIGS. 16 and 17 that is configured or arranged to receive and retain one or more sensors or sensor components or sensor arrangements for detecting or sensing one or more characteristics of the stream of gases flowing in the flow path. FIGS. 16 and 17 show the housing of the sensor assembly 60 without any sensors for clarity. The housing and sensors will be explained in further detail with references to FIGS. 19-24.

In this embodiment, the sensor housing is a modular component that is releasably secured, mounted, engaged, retained or fitted within the flow path so that it may be removed if desired for replacement, maintenance or repair. In this embodiment, the walls 56 and 54 of the flow path in the inlet section are discontinuous within a substantially straight section 61 of the flow path to thereby provide a receiving or mounting slot, aperture, recess or gap within which the sensor housing of the sensor assembly 60 may be received and retained. When installed, the housing of the sensor assembly bridges the retaining gap provided by the discontinuous walls 54, 56 so as to complete the flow path. With this configuration, the sensor assembly 60 is configured to provide sensing of one or more characteristic of the flow of gases in the bulk flow or primary flow path of the respiratory device. In other words, the sensor assembly 60 is not located in a separate chamber or secondary flow path relative to the bulk or primary flow path through the respiratory device.

In this embodiment, the sensor housing is configured to be received and retained within the mounting aperture of the flow path via a friction fit. However, it will be appreciated that any other releasable mounting configuration or retention system may alternatively be used, including a clipping system, latching system, snap-fit, or any other releasable configuration.

The sensor assembly 60 may be configured or adapted to mount one or more sensors for sensing one or more characteristics of the flow of gases in the flow path. Any suitable sensor may be mounted to the sensor housing as will be appreciated. In this embodiment, the sensor assembly at least comprises a gas composition sensor for sensing or measuring the gas composition or concentration of one or more gases within the gases stream. In this embodiment, the gas composition sensor is in the form of an ultrasound gas composition sensor system that employs ultrasonic or acoustic waves for determining gas concentrations. In particular, the ultrasound gas composition sensor utilizes binary gas sensing or analysis for determining the relative gas concentrations of two gases in a binary gas mixture. In this embodiment, the gas composition sensor is configured to measure the oxygen fraction in the bulk gases stream flow, which consists of atmospheric air augmented with supplemental oxygen, which is essentially a binary gas mixture of nitrogen ($N_2$) and oxygen ($O_2$). It will also be appreciated that the ultrasonic gas concentration sensor may be configured to measure the gas concentrations of other augmentation gases that have blended with atmospheric air in the gases stream, including nitrogen ($N_2$) and carbon dioxide ($CO_2$), or any other ratio of two gases. For example, the ultrasonic gas concentration sensor may be configured to measure carbon dioxide ($CO_2$) and deliver controlled carbon dioxide levels to the patient to control the patient's breathing pattern. By adjusting the carbon dioxide levels to the patient, the Cheyne-Stokes respiration of the patient can be controlled. Controlling the patient's breathing pattern can be useful in some situations, such as for athlete training to mimic high altitude conditions.

As previously described, in this embodiment, the respiratory device 10 comprises a gases inlet assembly 20 that is configured to receive ambient atmospheric air and a supplementary gas, such as oxygen from an oxygen supply line or gas bottle. However, it will be appreciated that the air supply need not necessarily be ambient and the air may be supplied to the gases inlet assembly from an air supply line or gas bottle. Further, it will be appreciated that the respiratory device 10 need not necessarily receive a supply of air. The respiratory device 10 may be configured to receive a supply of any two or more suitable gases for blending and subsequent delivery to the end user via a patient interface. The gases may be supplied to the gases inlet assembly of the respiratory device by any suitable means, including from central gases supply lines, gas bottles, or otherwise.

In this embodiment, the sensor assembly 60 also comprises a temperature sensor that is configured to measure the temperature of the gases stream and a flow rate sensor that is configured to sense the flow rate of the gases stream in the flow path.

Direct Inlet Flow Path-Second Embodiment

Figure 18A:
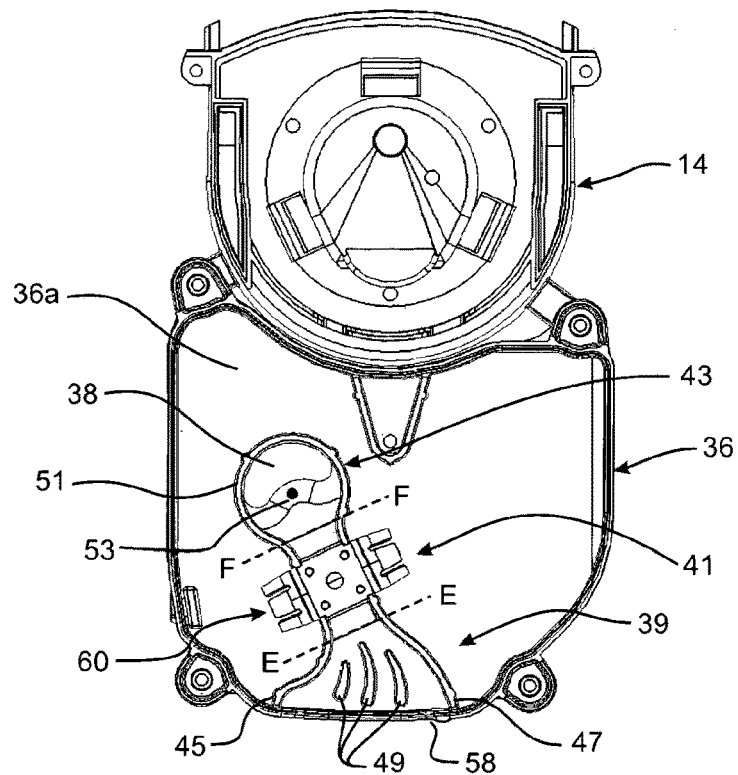
FIG. 18A shows an underside view of the respiratory apparatus of FIG. 12, showing a sensor assembly and a second embodiment of an inlet section of the gases stream flow path having a direct flow path.
Figure 18B:
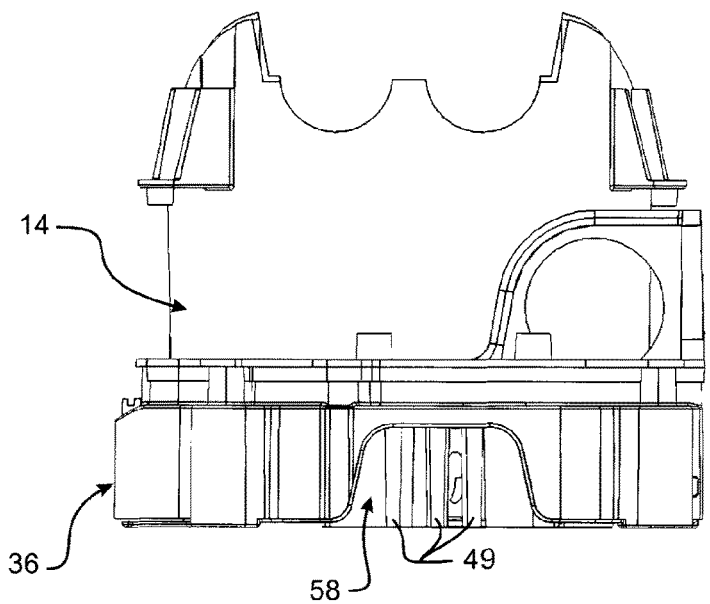
FIG. 18B shows a rear end elevation view of the respiratory assistance apparatus of FIG. 18A with the direct inlet flow path.
Figure 18C:
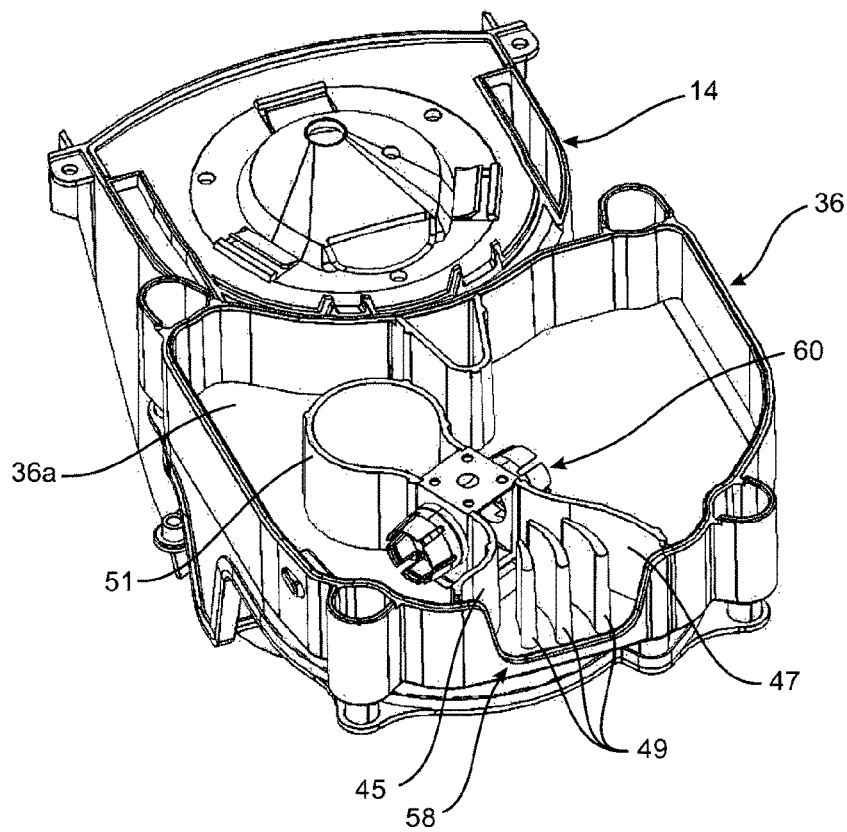
FIG. 18C shows a perspective view of the underside of the respiratory apparatus of FIG. 18A.

Referring to FIGS. 18A-18C, a second embodiment of the inlet section of the gases stream flow path in the base compartment 36 will be described. Like reference numerals in the drawings represent like components with respect to the first embodiment spiral inlet flow path described with references to FIGS. 14-17. In this second embodiment, the inlet section of the flow path is a shorter and more direct flow path between the inlet aperture 58 and exit port 38 of the base compartment 36. The shorter and more direct flow path reduces gas residence time in the base compartment, which reduces gas heat-up caused by the surrounding electronic components.

In this embodiment, the inlet flow path can be defined by three main zones or regions extending between the inlet aperture 58 and exit port 38. The three regions are an inlet zone 39, a sensor zone 41, and a transition zone 43.

Referring to FIG. 18A, the inlet zone or region 39 extends between the inlet aperture 58 and approximately the transition line EE prior to the sensor zone 41. In this embodiment the inlet zone 39 of the inlet flow path is defined between two walls 45, 47 which extend from at or toward the inlet aperture 58 and through to the sensor assembly 60. In this embodiment, the cross-sectional area of the inlet zone 39 gradually diminishes or reduces from the inlet aperture 58 toward the transition line EE into the sensor zone 41, such that the profile of the walls in the inlet zone forms a funnel-like configuration. For example, the side walls 45 and 47 have a wider displacement from each other at the inlet aperture 58 relative to their displacement from each other at or toward the transition line EE. In other words, this distance or displacement between the side walls 45,47 reduces from the inlet aperture 58 to the transition line EE such that the inlet zone 39 starts with a wide opening at the inlet aperture 58 and the flow path narrows progressively toward the transition line EE prior to the sensor zone 41. This funnel-like configuration of the inlet zone creates an accelerating gases stream flow, which promotes a more stable gas flow in the subsequent sensor zone.

Optionally, the inlet zone 39 may be provided with one or more flow directors 49. In this embodiment, the inlet zone 39 comprises a bend in that it is not a straight flow path directly from gases inlet assembly to the sensor zone, and this may generate an uneven flow or velocity gradient across the inlet flow path in one or more regions of the inlet flow path. To counteract this, the inlet zone 39 is provided with a plurality of flow directors 49 that are in the form of arcuate or curved fins (more clearly seen in FIG. 18C) which are configured or provided with a profile or shape that assists in promoting an even air flow into the sensor zone 41 that is not biased toward any particular wall of the flow path. It will be appreciated that the number and shape or profile of the flow directors 49 may be varied to assist in directing the air flow at the desired angle into the sensor zone 41, but preferably the bulk flow is configured to enter the sensor zone at a substantially perpendicular direction relative to the transition line EE or front opening of the sensor assembly 60. In this embodiment, the fins 49 assist in providing a stable flow through the sensor zone 41. Referring to FIG. 18B, the fins 49 may also function as tamper guards or protection guards to prevent assess by a user to the sensor assembly 60 which may contain sensitive or calibrated sensor components. In this embodiment the fins 49 are integrally formed and suspended down into the inlet zone from the upper lid 36a of the base compartment 36, although it will be appreciated that the fins may alternatively be integrally formed with or attached so as to extend up into the inlet zone from the base or underside portion 26a of the lower housing part 26. It will also be appreciated that the fins need not necessarily be vertically oriented, but may alternatively be horizontally oriented such that they extend from the side walls of the inlet zone of the inlet flow path, or oriented at any other suitable angle or mixtures of angles.

The sensor zone 41 is defined between the end of the inlet zone at approximately transition line EE to the start of the transition zone 43 at approximately transition line FF. The sensor zone comprises a modular removable sensor assembly 60 of the type previously described with reference to FIGS. 15-17 and which is situated in-line with the bulk flow path for sensing various characteristics or parameters of the gases stream. As shown, the terminating portion of the side walls 45, 47 extend into the front opening side of the sensor assembly 60 and the terminating portions of a loop wall 51 of the transition zone 43 extends into the opposite rear exit side of the sensor assembly 60. In a similar manner to the embodiment described with reference to FIGS. 15-17, the sensor assembly 60 is releasably retained within a retaining gap provided or formed between the terminating portions of the side walls 45, 47 and the loop wall 51.

The transition zone 43 is defined by a substantially curved perimeter or loop wall 51 that may substantially conform to at least a substantial portion of the circumference of a circle, or which is otherwise curved or concave in shape when viewed in plan. In this embodiment, the loop wall 51 may extend circumferentially about centre point 53. The opening into the transition zone 43 is defined by the terminating portions of the loop wall that extend outwardly relative to the centre point 53 for engaging with exit side of the sensor assembly 60. As shown, the substantially circular or bulbous transition zone 43 comprises an outlet for the air flow through exit port 38 provided in the upper lid 36a of the base compartment 36.

As with the spiral inlet flow path embodiment described with reference to FIGS. 14-17, the shorter direct inlet flow path of FIGS. 18A-18C is also enclosed from above and below by horizontally extending upper and lower walls or surfaces to form an enclosed channel or air flow passage. The flow path is primarily defined by the co-extending side walls 45,47 and loop wall 51, and these side walls are enclosed from above and below for example by the upper lid 36a of the base compartment and the base or underside portion 26a of the lower housing part 26 of the main housing (see FIG. 7). As shown, in this embodiment the side walls 45, 47, 51 are upright and extend substantially perpendicularly or vertically relative to the substantially horizontal enclosing upper lid 36a of the base compartment and underside portion 26a of the lower housing part 26.

Sensor Housing and Location

In the above embodiments, the sensor assembly 60 is located in a sensor zone with the inlet section of the flow path prior to the blower unit. However, the sensor assembly may also be alternatively located in a sensor zone situated in any other suitable part of the flow path prior to the humidification unit. In particular, the sensor zone of the flow path may be located at any location in the flow path upstream of (i.e., prior to) the humidification unit, including either before or after the blower unit.

The sensor housing and sensors of the sensor assembly 60 will now be described in further detail. The sensor assembly may be employed in either of the spiral or direct inlet flow path embodiments described with reference to FIGS. 14-18C. Referring to FIGS. 19-23, the sensor assembly 60 comprises a sensor housing 62 to which one or more sensors are mounted for measuring various characteristics of the gases stream in the bulk flow path. In this embodiment, the sensor housing 62 comprises a central main body 63 that extends between a first end 74 and second end 76. The main body 63 is hollow and has openings at both ends such that it provides a passageway or sensing passage 86 for the gases stream to pass through from the first end 74 to the second end 76 of the main body 63. In particular, the gases stream flows generally in the direction of the flow axis 110 shown in FIG. 20 that extends from the first end 74 to the second end 76 of the main body 63.

In this embodiment, the main body 63 is formed between the first 74 and second 76 ends by two spaced-apart vertical side walls 64 and 66, and upper 68 and lower 70 walls that extend horizontally between the vertically extending side walls 64, 66, and where the walls collectively form and define the sensing passage. The main body is open at both ends 74,76 which in use are aligned with the flow path direction such that gases stream travels through the hollow interior or cavity of the main body defined by the inner surfaces of the side, upper and lower walls. In this embodiment, the width W between the side walls 64, 66 and the height (H) between the upper and lower walls 68, 70 substantially corresponds to the cross-sectional dimensions of the portion or section of the flow path immediately surrounding either side of the sensor assembly.

Mounting of Sensors
Temperature and Flow Rate Sensors

Figure 19:
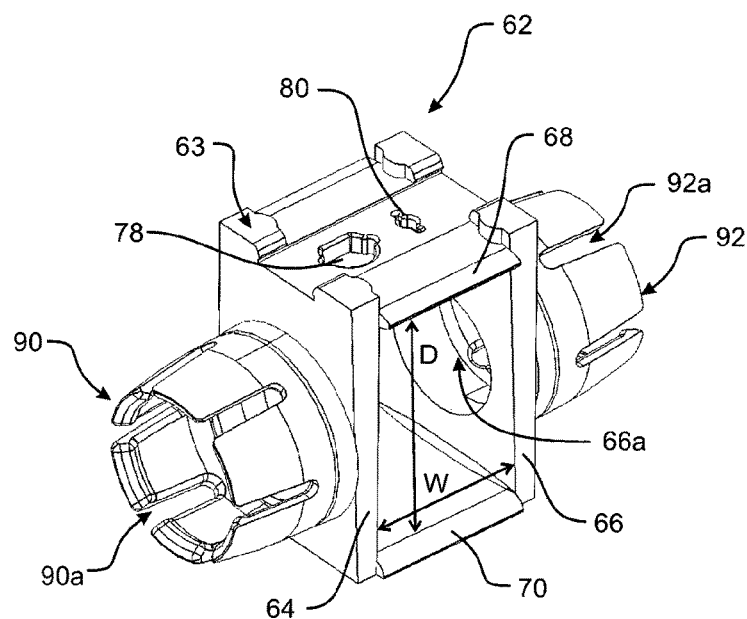
FIG. 19 shows a perspective view of a housing of a sensor assembly in accordance with an embodiment of the invention.
Figure 20:
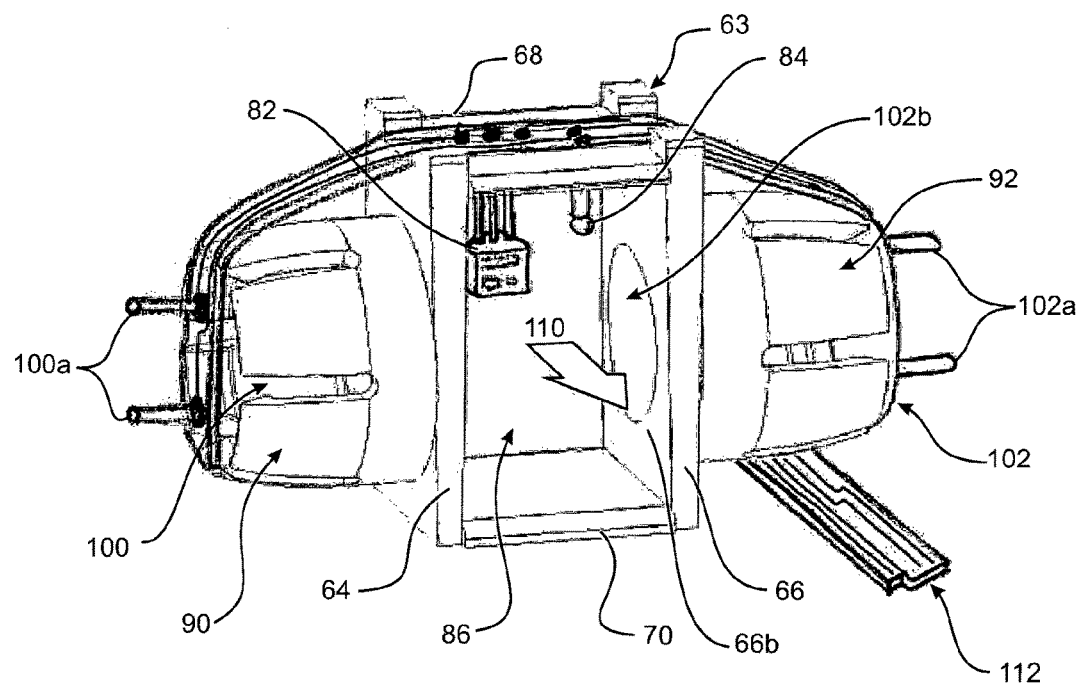
FIG. 20 shows a perspective view of the sensor assembly housing of FIG. 19 with an arrangement of sensors mounted to the housing.
Figure 21:
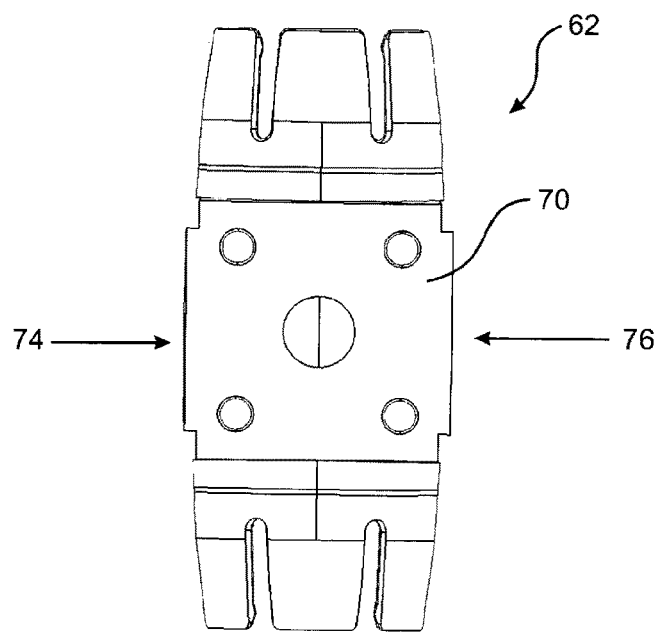
FIG. 21 shows an underside view of the housing of the sensor assembly of FIG. 19.
Figure 22:
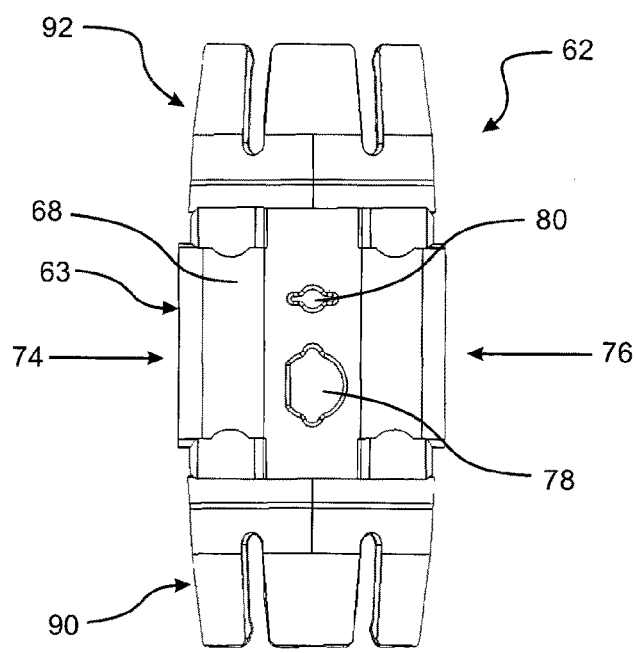
FIG. 22 shows a plan view of the top side of the housing of the sensor assembly of FIG. 19.

Referring to FIGS. 19, 20 and 22, this embodiment of the sensor assembly is provided with mounting apertures 78, 80 for receiving and retaining a temperature sensor 82 and flow rate sensor 84. For example, a temperature sensor mounting aperture 78 is provided in the upper wall 68 of the main body of the sensor housing and is configured to receive and retain a temperature sensor. Likewise, a separate flow rate sensor mounting aperture 80 is provided in the upper wall 68 of the main body 63 of the sensor housing 62 and is shaped or configured to receive and retain a flow rate sensor. The sensors 82, 84 may be held within their respective mounting apertures 78, 80 by friction fit, snap fit or any other coupling or fixing configuration. The temperature sensor may also optionally be provided with infra-red radiation shielding components.

Referring to FIG. 20, the temperature sensor 82 and flow rate sensor 84 are mounted such that they are suspended down into sensing passage 86 from the upper wall 68 of the main body 63. Preferably, the temperature sensor 82 and flow rate sensor 84 are suspended substantially centrally between the ends 74, 76 of the main body. The sensors 82, 84 need not necessarily be suspended from the upper wall and need not necessarily be vertically oriented. In other embodiments, the sensors 82, 84 may be mounted or secured to any of the upper, lower or side walls of the main body 63 of the sensor housing. Further, the orientation of the sensors 82, 84 into the sensing passage from their support or mounting wall may be vertical, horizontal, or any other suitable angle. The sensors 82, 84 need not necessarily be centrally located relative to their support wall, but may be located at any suitable position within the sensing passage, central or otherwise. The sensors 82, 84 may also extend from the same or different support walls.

In this embodiment, the temperature sensor 82 may be a monolithic, digital, IC, temperature transmitter, but any alternative type of temperature sensor, whether analogue or digital, may be employed. In this embodiment, the temperature sensor 82 is a silicon band-gap temperature transmitter.

In this embodiment, the flow rate sensor 84 comprises a hot-wire anemometer (HWA) flow detector. In one form, the flow rate sensor 84 is a constant-resistance HWA in which the detector comprises a controlled temperature heated bead thermister located in the sensing passage and from which the flow rate can be determined based on the energy (current) required to maintain the bead at a preset temperature. The preset temperature is preferably configured to be set to a level that does not alter the local temperature of the gases stream flowing in the sensing passage appreciably in the context of O2 measurement. It will be appreciated that in other forms, the flow rate sensor 84 may comprise a constant-current HWA in which flow rate is determined from the change in resistance of the heated bead. It will be appreciated that any other suitable form of flow rate sensor or detector may be used if desired.

Ultrasound Gas Composition Sensor System

In this embodiment, the ultrasound gas composition sensor is implemented and configured to sense the relative gas concentrations of a binary gas mixture in the gases stream using binary gas analysis based on a non-invasive cross-flow beam, pulse or wave of ultrasound energy, as will be explained in further detail later.

The sensor housing comprises transducer mounting assemblies generally indicated at 90 and 92 for receiving and retaining ultrasonic transducer components of the ultrasound gas composition sensor system. In this embodiment, the transducer mounting assemblies 90, 92 are provided on opposite sides of the main body 63 such that they support or mount a pair of transducers on opposite sides of the sensing passage 86. The transducers are aligned with, and face each other across, the sensing passage 86. The transducer mounting assemblies 90, 92 are mounted or fixed to a respective side wall 64, 66 of the main body. Each transducer mounting assembly or formation is configured to provide a retaining cavity 90a, 92a that is dimensioned and shaped to receive and retain a complementary dimensioned and shaped transducer component of the gas composition sensor system. In this embodiment, the receiving cavities 90a, 92a are substantially cylindrical and are aligned or coaxial with circular transducer apertures provided through each of the side walls 64, 66 of the main body. FIG. 19 shows a transducer aperture 66a of side wall 66, and side wall 64 similarly has a corresponding transducer aperture, although it is not visible. It will be appreciated that the transducer pair could in alternative embodiments be mounted in the upper 68 and lower 70 walls of the main body, with the remaining temperature and flow rate sensors 82,84 being mounted to extend into the sensing passage from either side wall 64,66.

Figure 23:
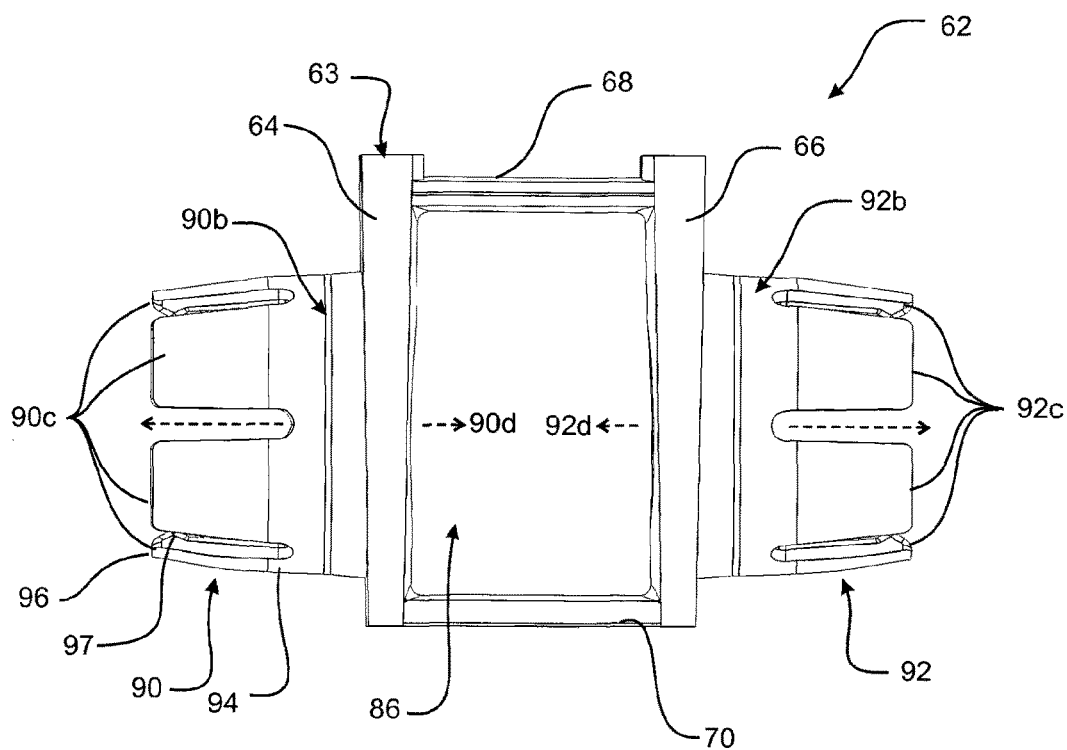
FIG. 23 shows a side elevation view of the housing of the sensor assembly of FIG. 19.
Figure 24:
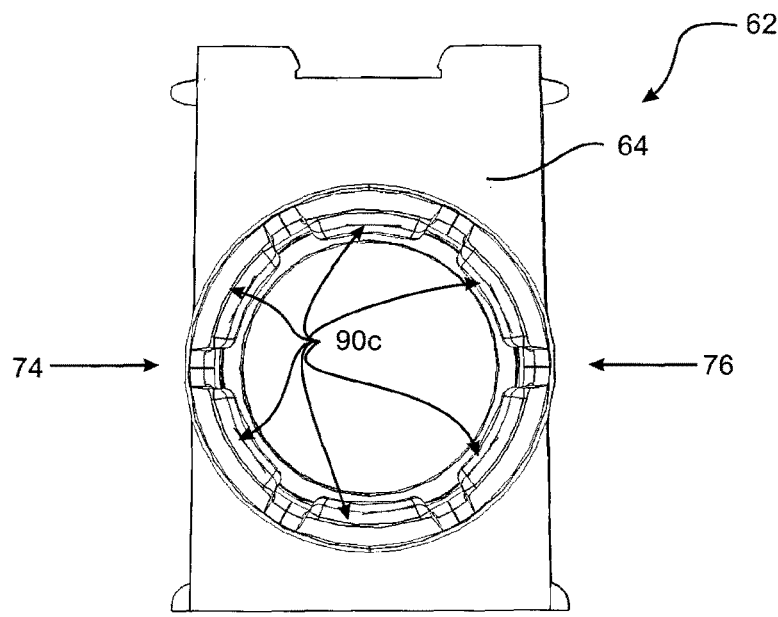
FIG. 24 shows an end elevation view of the housing of the sensor assembly of FIG. 19.

Referring to FIGS. 23 and 24, in this embodiment each transducer mounting assembly 90, 92 has a cylindrical base portion 90b, 92b that is fixed or mounted at one end to a respective outer surface of a respective side wall 64, 66 of the main body 63, and at the other end is provided with at least one pair of opposed clips or clipping portions or fingers 90c, 92c extending from the cylindrical base portion. The cylindrical base portion in combination with the extending clips collectively defines the retaining cavity 90a, 92a within which the transducer component is securely received and retained. In this embodiment, each transducer mounting assembly is provided with a circular array of clips or clipping portions 90c, 92c that are interspaced about the entire circumference of the cylindrical base portion 90*b*, 92*b*. In this embodiment, six clipping portions 90*c*, 92*c* forming three opposed pairs are provided, but it will be appreciated that the number of pairs of clipping portions may be varied if desired.

The clipping portions 90*c*, 92*c* may be resiliently flexible such that they may be flexed slightly outwardly relative to their respective receiving cavity 90*a*, 92*a* axis indicated at 90*d*, 92*d* respectively. The clipping portions 90*c*, 92*c* may also be configured to taper in direction toward their respective cavity axis 90*d*, 92*d* as they extend away from their respective cylindrical base portions 90*b*, 92*b*. This provides a cylindrical retaining cavity with reducing or gradually tapering diameter as it extends away from the base portion 90*b*, 92*b*. As shown in FIG. 24, each clipping portion 90*c*, 92*c* is substantially arcuate or concave in shape when viewed in cross-section along its length extending away from its associated cylindrical base portion 90*b*, 92*b* such that it conforms to a circumferential portion of a cylinder. Referring to FIG. 23, by way of example each clipping portion extends between a first end 94 located at the cylindrical base portion 90*b* and a second or terminating end 96 which defines the end of the transducer receiving cavity 90*a*. In this embodiment, the inner surfaces toward terminating end 96 of each clipping portion are provided with a ridge or shoulder portion 97 that extends into the retaining cavity and which is configured to act as a stop or grip formation for securing the transducer component within its retaining cavity.

When installing the transducer components, which are typically cylindrical in shape, within their respective transducer mounting assemblies 90, 92, the clipping portions 90*c*, 92*c* flex slightly outwardly upon partial insertion of the transducer components and then revert to their rest state upon full engagement of the transducers within the cavities to thereby securely grip or hold the transducer within its respective retaining cavity.

It will be appreciated that other transducer mounting assemblies could alternatively be used to receive and retain the transducer elements within the sensor housing if desired. Preferably, the transducer mounting assemblies are configured to allow the transducer components to be releasably secured, such that the transducers can be removed from the sensor housing for replacement or repair if desired.

In this embodiment, the main body 63 and transducer mounting assemblies are integrally formed with each other from a suitable material, such as plastic. However, it will be appreciated that the parts of the sensor housing may be formed separately and then fixed or connected together.

Referring to FIG. 20, transducers 100, 102 are shown installed in their respective transducer mounting assemblies 90, 92 of the sensor housing. In this embodiment, the transducers and transducer mounting assemblies are configured to cooperate such that the front surfaces of the transducers extend into their respective transducer apertures in the side walls 64,66 of the main body 63 such that they sit flush with the remaining inner surfaces of the side walls. For example, with reference to FIG. 20, the front surface 102*b* of transducer 102 is shown to be substantially flush with the inner surface 66*b* of the side wall 66. The same configuration is provided for the opposing transducer component 100.

As shown, this configuration provides a pair of transducers 100,102 that are aligned and facing each other from opposite sides of the sensing passage 86 of the main body 63 such that ultrasound waves are transmitted in a direction that is substantially perpendicular to the direction or flow axis 110 of the flow of gases travelling through the passage 86 from the first end 74 to the second end 76 of the main body.

The distance (e.g. indicated by W in FIG. 19) between the pair of transducers 100,102, which defines the acoustic beam path length, is selected to be large enough to provide the desired sensitivity but short enough to avoid phase wrap-around ambiguity. For example, the distance between the transducers is selected to be large enough to increase sensitivity, but is limited based on the total phase shift expected for the range of gas compositions and temperatures being sensed.

Sensor Control System and Circuitry

Referring to FIG. 20, the electrical terminals or connectors 100*a*, 102*a* of the transducers 100, 102 protrude out from the sides of the main body 63 of the sensor housing and the electrical terminals 82*a*, 84*a* of the temperature and flow rate sensors 82,84 are accessible at the outer surface of the upper wall 68 of the main body 63. A flexible wiring loom or tape 112 may extend across the sides and upper surface of the sensor housing to provide wiring connections to the electrical terminals of the sensors. The wiring 112 extends to the sensor control system and circuitry of the respiratory device 10 which is configured to control the sensors, as will now be described in further detail.

Figure 25:
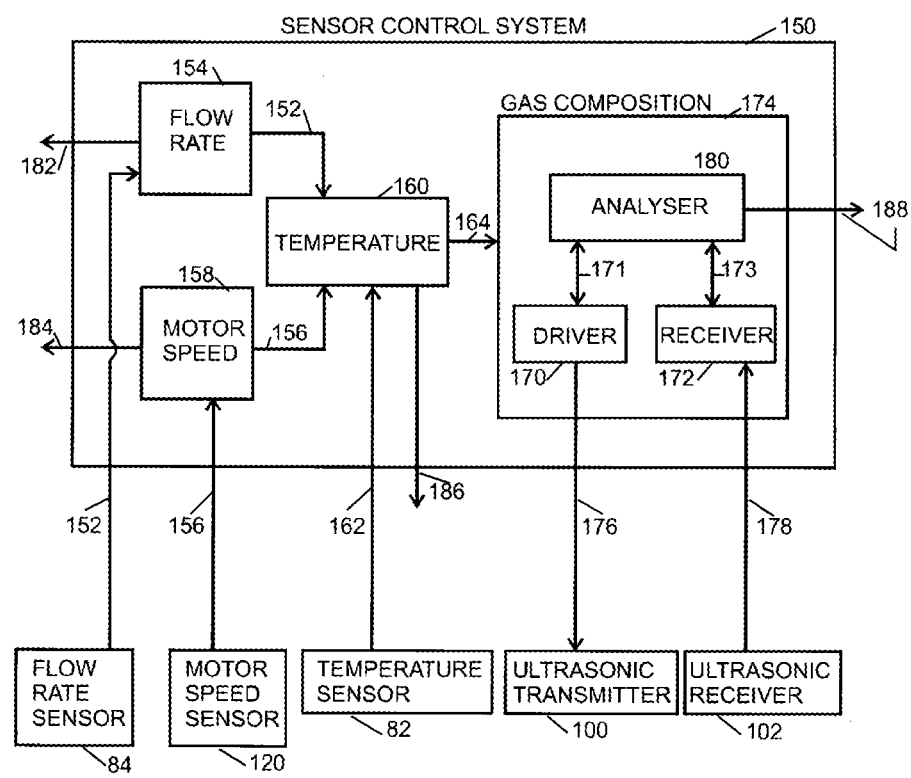
FIG. 25 shows a block diagram of a sensor control system of the respiratory assistance apparatus in accordance with an embodiment of the invention.

Referring to FIG. 25, an example of the sensor control system 150 that is electrically connected via the wiring 112 to the sensor components 100,102,84, and 82 will be described by way of example. It will be appreciated that the electronic sensor control system 150 may be implemented in software or hardware, including implementation on any programmable device such as a microprocessor, microcontroller, Digital Signal Processor or similar, and which may have memory and associated input and output circuitry as will be appreciated. It will be appreciated that the various modules of the sensor control system 150 may be varied or separated further or integrated and FIG. 25 will be described by way of example only as to the general functionality of the sensor control system. The sensor control system 150 may be integrated with the main control system of the respiratory device or may be a separate sub-system that communicates with the main controller or control system. The sensor control system 150 will be described with reference to a particular arrangement or configuration of sensors that are arranged for determining the gas composition or relative concentrations of gases in a binary gas mixture, such as an air/oxygen mixture, which is substantially equivalent to a nitrogen/oxygen mixture. However, it will be appreciated that the sensor control system may be adapted to provide information indicative of other gas concentrations within the gases stream.

Flow Rate Module

The flow rate sensor 84 is configured to sense the flow rate, for example in Litres per minute, of the gases stream 110 flowing through the sensing passage 86 of the sensor housing and generate a representative flow rate signal 152 that is received and processed by flow rate module 154 in the sensor control system 150. A motor speed sensor 120 is also preferably provided in the blower unit for sensing the motor speed, for example in revolutions per minute (rpm) of blower unit motor. The motor speed sensor 120 generates a representative motor speed signal 156 that is received and processed by motor speed module 158.

Temperature Module

A temperature module 160 is configured to receive and process a temperature signal 162 that is generated by the temperature sensor 82 which represents the temperature of the gases stream flowing through the sensing passage 86 of the sensor housing. In this embodiment, the temperature sensor 82 is configured to sense the temperature of the gases stream in the vicinity of the acoustic beam path between the transducers 100, 102.

The temperature module 160 is optionally configured to apply temperature compensation to the temperature signal 162 to compensate for potential errors or offsets generated by the temperature sensor 82. In particular, as the sensor assembly 60 is located below the blower unit compartment and other electronic circuitry, heat from the circuitry and motor, depending on the operating conditions, can impact on the temperature as sensed by the temperature sensor 82. For example, due to the heat above the sensor assembly, the temperature signal 162 may indicate a gas stream temperature that is higher than the true temperature. To compensate for this potential error when in certain operating conditions, the temperature module 160 is configured to apply a temperature compensation factor or correction based on the following formula: Tcorrected=Tsensor+$\Delta$T, where: Tcorrected is the corrected temperature after compensation, Tsensor is the temperature as sensed by the temperature sensor 82 as represented by signal 162, and $\Delta$T is the calculated or predicted temperature error based on the current operating conditions of the respiratory device.

The temperature error ($\Delta$T) will vary depending on the operating conditions of the respiratory device 10. In this embodiment, the temperature error is calculated based on a proportional relationship with the system conditions relating to the current flow rate 152 of the gases stream in the respiratory device and the current motor speed 156. Typically, an increased flow rate has a cooling effect while increased motor speed causes increased heating within the housing of the respiratory device due to higher power usage. In operation, the temperature module is configured to continuously or periodically calculate the temperature error $\Delta$T based on the current system operating conditions, and in particular, the current flow rate 152 and motor speed 156. The updated temperature error $\Delta$T is then applied to the incoming sensed temperature, Tsensor 162 from the temperature sensor to generate the corrected temperature, Tcorrected.

In one embodiment, $\Delta T=\alpha\times$(motor speed/flow rate), where $\alpha$ is a constant. However, it will be appreciated that $\Delta$T may alternatively be calculated based on a look-up table or other algorithm which takes into account one or more other operating conditions or system variables relating to the operation of the respiratory device and which have an impact on the temperature variation that is likely to occur in the vicinity of the temperature sensor 82. In some embodiments, $\Delta$T may incorporate time dependent effects which have an impact on the temperature variation, such as heat storage in the respiratory device during long run periods. For example, $\Delta$T may also be expressed as an integro-differential equation to express time variant effects such as those caused by thermal capacitance of one or more parts of the respiratory device.

Gas Composition Module

The gas composition sensor system is configured as an ultrasound binary gas sensing system. As mentioned, the gas composition sensing system in this embodiment comprises a pair of ultrasonic transducer components 100, 102 that are provided on opposite sides of the sensing passageway of the sensor housing. One of the transducer components 100 is configured as an ultrasonic transmitter for transmitting a unidirectional ultrasound or acoustic beam wave or pulse across the passageway in a direction substantially perpendicular to the direction of the gases flow stream through the sensing passage to the other ultrasonic transducer which is configured as an ultrasonic receiver to receive the transmitted ultrasonic wave or pulse on the other side of the passage. In this embodiment, the transducer components 100, 102 may be piezo-ceramic transducer elements, typically operating at a narrow bandwidth, or any other suitable operable ultrasonic transducer elements. In this embodiment, the transducer elements operate at a frequency of approximately 25 kHz, although this may be varied as desired. In preferred forms, the operating frequency is selected to be above the human audible acoustic spectrum so that the gas composition sensing is silent to the user and/or at a high enough frequency to reduce or minimise interference from noise sources.

The ultrasonic transmitter 100 and receiver 102 are controlled respectively by driver 170 and receiver 172 circuitry of the gas composition module 174. In particular, the driver circuitry 170 provides a control excitation signal 176 to the ultrasonic transducer to drive it to transmit pulses of ultrasonic energy. The ultrasonic receiver 102 senses the pulse and generates a representative reception signal 178 that is received and processed by its receiver circuitry 172. While a pulsed system is utilized in this embodiment, a continuous wave or standing wave approach may be employed in alternative embodiments.

Binary gas analysis using ultrasound is based on sensing the speed of an acoustic pulse through the gas sample, which in this case is the bulk or primary flow of the gases stream flowing through sensing passage 86 of the sensor housing. The speed of sound is a function of gas mean molecular weight and temperature. In this configuration, the gas composition module 174 receives a temperature signal 164 from the temperature module 160 representing an indicative temperature of the gases flowing between the beam path between ultrasonic transducers. With knowledge of sensed speed of sound and sensed temperature, the gas composition in the gases stream may be determined or calculated. In particular, measurements of the speed of sound across the sensing passage may be used to infer the ratios of two known gases by reference to empirical relationships, standard algorithms, or data stored in the form of look-up tables, as is known in the art of binary gas analysis with ultrasound. It will be appreciated that alternatively an estimate of the temperature of the gases stream in the beam path of the ultrasound transducers may be used in the binary gas analysis calculations if a temperature sensor is not employed. In such alternative embodiments, the temperature of the gases stream may be conditioned or controlled to within a narrow temperature band to enable an estimate of temperature of the gases stream in the beam path to be used.

In some embodiments, the respiratory device may also be provided with a humidity sensor that is located in the flow path and which is configured to generate a humidity signal indicative of the humidity of the gases stream flowing through the sensor assembly. In such embodiments, the gas composition may be determined by the sensed speed of sound, and the sensed temperature and/or sensed humidity. The humidity sensor may be a relative humidity sensor or an absolute humidity sensor. In some embodiments, the gas composition may be determined based on the sensed speed of sound and the sensed humidity, without the need for a temperature sensor.

The gas composition sensing system may be used to measure respective ratios of any two known gases in a gas composition. In this embodiment, the gas composition module is configured to determine the relative gas concentration in a mixture of air blended with supplementary oxygen, which is substantially equivalent to a nitrogen/oxygen mixture. In such a binary gas mixture, by monitoring the speed of sound and taking the temperature into account, the mean molecular weight of the gas can be determined, and thus, the relative concentrations of the two gases may be determined. From this ratio, the oxygen fraction or nitrogen fraction of the gases stream may be extracted.

In this embodiment, the gas composition module 124 comprises an analyser or controller 180 that is configured to operate the ultrasonic transducers 100, 102 via their respective driver 170 and receiver 172 circuitry with control signals 171, 173. The analyser 180 is also configured to receive and process the corrected temperature signal 164 from the temperature module 160. In operation, the analyser 180 is configured to periodically at a desired frequency transmit unidirectional ultrasonic or acoustic pulses across the sensing passage to determine the speed of sound of the acoustic pulses. The measure of speed of sound is then used to determine the gas composition with knowledge of the temperature from the temperature module 160. The speed of the acoustic pulse may be determined in any desired manner, including using timer circuitry to determine the transit time of the acoustic pulse to travel across the passageway from the transmitter 100 to the receiver 102 either directly or indirectly via phase detection. It will be appreciated that phase can be tracked to minimise 'wrap-around' effects if suitable signal processing is implemented. The distance between the transducer elements 100, 102 is known and equivalent to the width (W in FIG. 19) between the side walls 64, 66 of the sensor housing and therefore the speed of sound can be determined based on the transit time and distance between the transducers (which corresponds to the beam path length). In particular, the analyser may be pre-programmed and calibrated with the data indicative of the distance between the transducers, and/or any other generally applicable or device specific characteristics useful in determining gas composition via speed of sound sensing. The calibration can take into account the change in distance between the transducer elements 100, 102 as a function of the temperature. For example, the distance between the side walls 64, 66 of the sensor housing may increase or decrease as the temperature changes.

Optionally, the gas composition sensor module may be configured with a user selectable or pre-programmed scale factor or correction factor to account for argon when determining the oxygen fraction, which is preferably used when oxygen is supplied to the respiratory device from a commercial oxygen concentrator that uses a pressure swing adsorption technique. For example, the user may activate the control system to employ the argon scale or correction factor to modify the sensed oxygen fraction to remove any argon component to yield the computed oxygen fraction.

The sensor control system 150 may output data or signals indicative of the various characteristics sensed by the sensor assembly or other sensors. For example, output signals or data 182, 184, and 186 from modules 154, 158, 160 may represent the sensed flow rate 182, motor speed 184, and temperature 186. Likewise, the gas composition module is configured to generate one or more output signals or data 188 indicative of the gas composition as sensed by the ultrasound gas compositions sensing system. In this embodiment, the output signal 188 may represent the oxygen fraction or oxygen (O2) concentration in the gases stream. Alternatively, the signal or an additional signal may represent nitrogen (N2) concentration or fraction. It will also be appreciated that the system may be modified to provide signals representing other gas concentrations within the gases stream, including, but not limited to, carbon dioxide (CO2) for example.

The gas concentration output signal or signals 188 may then be received and processed by the main controller of the respiratory device. For example, the main controller may be configured to display a sensed oxygen reading on an output display of the respiratory device based on the oxygen signal 188. In one embodiment, the user control interface 30 (see FIG. 8) may be configured to display a gas concentration reading, e.g. oxygen concentration or other one or more gas concentration levels, as sensed by the ultrasound gas composition sensor system.

In some embodiments, the main controller is configured to determine whether one or more gas concentration levels, for example the oxygen concentration, stays within user-defined ranges, defined by maximum and/or minimum thresholds. For example, in such embodiments, the main controller may be configured to compare the sensed gas concentration level based on the gas concentration output signal 188 to the user-defined or selected gas concentration level thresholds. If the sensed level is below the minimum threshold, or above a maximum threshold, or otherwise outside a user-defined range, the main controller may trigger or activate an alarm incorporated into the device, which may be audible, visual, tactile, or any combination of these. The main controller may optionally also shut-down the device or trigger any other appropriate operational functions appropriate to the respective, triggered alarm.

In some embodiments, the respiratory device 10 comprises a disinfection system and/or cleaning mode of the type described in WO 2007/069922, the contents of which are incorporated by reference. Such disinfection systems employ thermal disinfection by circulating heated dry gases through portions of the gases flow path to the user interface. In such embodiments, the main controller is configured to determine whether the oxygen concentration level in gases flow path is below a preset oxygen concentration level based on the sensed oxygen signal 188 prior to commencing any disinfection system or cleaning mode. For example, the main controller may be configured to prevent initiation of any cleaning mode until the sensed oxygen fraction is within a safe range, preferably below about 30%, to minimize fire hazards.

The oxygen signal 188 may additionally be used to automatically control the motor speed of the blower unit to alter the flow rate of the gases stream to thereby alter or modify the oxygen fraction to the desired level, or to halt operation of the device should the oxygen fraction move outside preset upper or lower thresholds. Alternatively, the user of the respiratory device may manually control the flow rate of the oxygen supply from the central gases source connected to the respiratory device to thereby vary the oxygen fraction based on real-time feedback from the displayed oxygen reading, without needing to estimate the oxygen fraction based on printed look-up tables. In some embodiments, the respiratory device may have a valve that automatically alters or modifies the flow rate of the oxygen supply from the central gases source to thereby vary the oxygen fraction. The main controller can receive the oxygen signal 188 and adjust the oxygen valve accordingly until a predetermined value for the oxygen signal 188 is reached, which corresponds to a desired oxygen fraction.

Alternative Ultrasound Gas Composition Sensor System Configurations

Referring to FIGS. 26A-26E, various alternative configurations of the ultrasonic transducers will be described for the gas composition sensing system for sensing the speed of sound through the gases stream by the transmission and reception of cross-flow ultrasonic beams or pulses. Like reference numerals, represent like components.

Referring to FIG. 26A, the transducer configuration 200 of the embodiment described above with reference to FIGS. 19-25 is schematically illustrated. As shown, the transducer configuration provides an arrangement in which there is a pair of transducers 202,204 opposing each from opposite sides of the sensing passage 206, with the air flow path direction indicated generally by 208. In this configuration 200, each of the transducers 202,204 is driven as either a dedicated transmitter or receiver, such that ultrasonic pulses 210 are transmitted uni-directionally across the air flow path from the transmitter to the receiver transducer. As shown, the transducer pair is aligned (i.e. not-displaced upstream or downstream from each other) relative to the air flow path direction 208 and is configured to transmit cross-flow pulses that are substantially perpendicular to the air flow path direction.

Referring to FIG. 26B, an alternative transducer configuration 220 is illustrated in which a pair of transducers 222,224 is provided opposing each other on opposite sides of the sensing passage, but wherein each transducer may operate as both a transmitter and receiver, i.e. is an ultrasonic transmitter-receiver or transceiver. In this configuration, bi-directional ultrasonic pulses 226 may be sent between the transducer pair 222,224. For example, pulses may be sent back and forth alternately between the transducers or in any other sequence or pattern. Again, the transducer pair is aligned relative to the air flow path direction and are configured to transmit cross-flow pulses that are substantially perpendicular to the air flow path direction.

Referring to FIG. 26C, an alternative echo transducer configuration 230 is illustrated in which the transmitter and receiver transducer pair is provided in the form of a single ultrasonic transmitter-receiver transducer 232 that is provided on one side of the sensing passage and which is configured to transmit cross-flow acoustic pulses 236 across the sensing passage 206 and receive the reflected pulse or echo reflected back from the opposite side of the sensing passage.

Referring to FIG. 26D, an alternative transducer configuration 240 is illustrated in which the transmitter transducer 242 and transmitter receiver 244 are displaced from one another relative to the air flow path direction (i.e. one is upstream from the other) and on opposite sides of the sensing passage. In FIG. 26D, the receiver is upstream from the transmitter, although an opposite configuration could be employed. With this arrangement, the transmitter 242 may either transmit direct cross-flow pulses across the sensing passage 206 to the receiver 244 as shown by beam 246, or may create a longer indirect path length by a reflected path comprising at least two reflections as indicated by beam 248. As shown, with this displaced configuration, the acoustic pulses have a cross-flow direction that is angularly traversing rather than substantially perpendicular to air flow path direction 208. It will also be appreciated that while a uni-directional configuration is shown, the transducers 242, 244 may alternatively be ultrasonic transmitter-receivers to enable bi-directional beam pulses to be transmitted back and forth between the transducers (i.e. both upstream and downstream relative to the air flow).

Referring to FIG. 26E, an alternative transducer configuration 250 is illustrated that is a modification of the configuration of FIG. 26D where the transmitter 252 and receiver 254 are again displaced from each other in the air flow direction 208 but where they are located on the same side of the sensing passage such that the transmitted cross-flow pulses 256 comprise at least one reflection (or multiple reflections for a longer path length) from the opposing side of the sensing passage 206. Otherwise, the same alternative options as that described with reference to FIG. 26D apply, including bi-directional operation and switching the location of the transmitter and receiver.

Figure 27A:
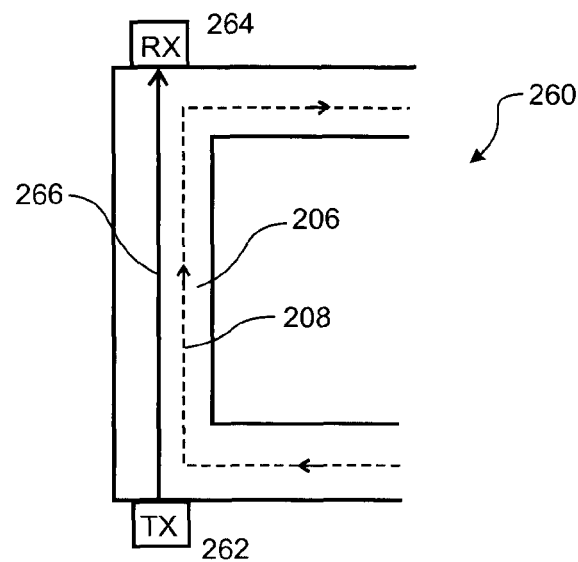
FIGS. 27A-27C show schematic diagrams of various ultrasonic transducer configurations for the sensor assembly using along-flow beams.
Figure 27B:
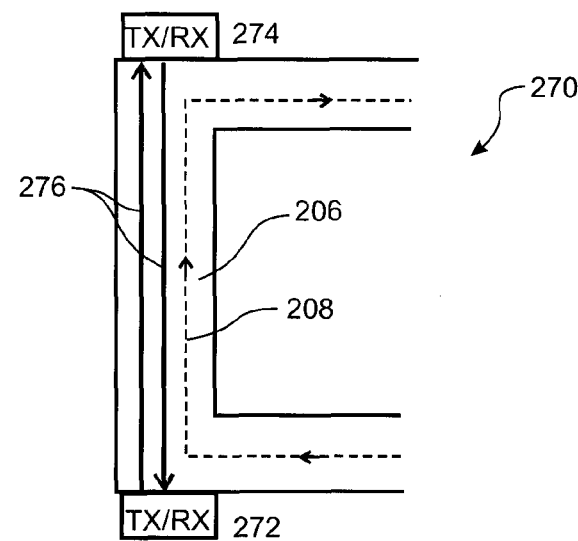
Figure 27C:
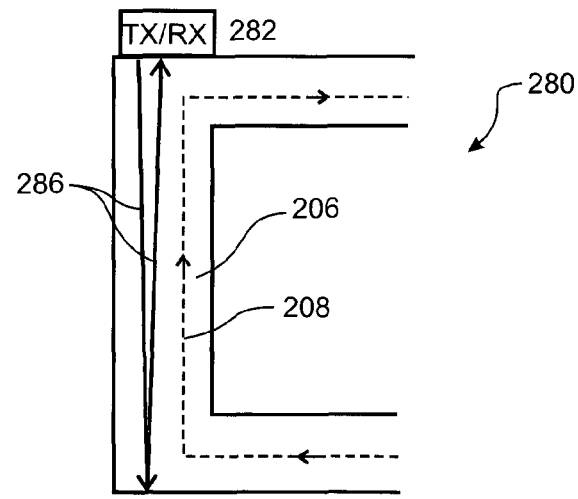

Referring to FIGS. 27A-27C, various further alternative configurations of the ultrasonic transducers will be described for the gas composition sensing system for sensing the speed of sound through the gases stream by the transmission and reception of along-flow ultrasonic beams or pulses. Like reference numerals represent like components.

Referring to FIG. 27A, an alternative transducer configuration 260 is illustrated in which there is a pair of transducers 262,264 opposing each other from opposite ends of the sensing passage 206, with the air flow path direction or axis indicated generally by 208. In this configuration 260, each of the transducers 262,264 is driven as either a dedicated transmitter or receiver, such that along-flow ultrasonic pulses 266 are transmitted uni-directionally in a beam path between the transmitter and receiver that is substantially aligned or parallel with the gases flow path axis 208 in the sensing passage 206. In the embodiment shown, the transmitter is upstream of the receiver, but it will be appreciated that the opposite arrangement could be employed. With this configuration, a flow rate sensor is provided in the sensing passage to provide a flow rate signal indicative of the flow rate of the gases stream in the sensing passage. It will be appreciated that the speed of sound in the sensing passage can be derived or determined in a similar manner to that previously described with the previous embodiments, and that the flow rate signal is utilized in the signal processing to remove or compensate for the gases flow rate in the calculated speed of sound signal.

Referring to FIG. 27B, an alternative transducer configuration 270 is illustrated in which a pair of transducers 272,274 is provided opposing each other from opposite ends of the sensing passage like in FIG. 27A, but wherein each transducer may operate as both a transmitter and receiver, i.e. is an ultrasonic transmitter-receiver or transceiver. In this configuration, bi-directional along-flow ultrasonic pulses 276 may be sent between the transducer pair 272,274. For example, pulses may be sent back and forth alternately between the transducers or in any other sequence or pattern. Again, the transducer pair are aligned with the air flow path axis 208 and are configured to transmit cross-flow pulses in a beam path or paths that are substantially aligned or parallel to the air flow path axis 208 in the sensing passage 206. With this configuration, a separate flow rate sensor need not necessarily be provided, as the flow rate component of the speed of sound signal can be directly derived or determined from processing of the transmitted and received acoustic pulses.

Referring to FIG. 27C, an alternative echo transducer configuration 280 is illustrated in which the transmitter and receiver transducer pair is provided in the form of a single ultrasonic transmitter-receiver transducer 282 that is provided at one end of the sensing passage (whether at the start or end) and which is configured to transmit along-flow acoustic pulses 286 along the sensing passage 206 in a beam path substantially aligned or parallel to the air flow axis 208 and receive the reflected pulse or echo reflected back from the opposite end of the sensing passage. In the embodiment shown, the transmitter-receiver 282 is shown at the end of the passage, but it could alternatively be located at the start of the passage. Like the configuration of FIG. 27A, a flow rate sensor is provided in the sensing passage to enable the speed of sound calculation to compensate for the air flow rate component.

With the alternative configurations of FIGS. 26B-26E and 27A-27C, it will be appreciated that the driver and receiver circuitry, and signal processing, can be adapted accordingly for the sensing of the speed of sound in the sensing passage, which is then in turn used to determine the gas composition as previously explained.

Preferred Features:

1. A respiratory assistance apparatus configured to provide a heated and humidified gases stream, comprising: a gases inlet configured to receive a supply of gases; a blower unit configured to generate a pressurised gases stream from the supply of gases; a humidification unit configured to heat and humidify the pressurised gases stream; a gases outlet for the heated and humidified gases stream; a flow path for the gases stream through the respiratory device from the gases inlet through the blower unit and humidification unit to the gases outlet; a sensor assembly provided in the flow path before the humidification unit, the sensor assembly comprising an ultrasound gas composition sensor system for sensing one or more gas concentrations within the gases stream.

2. A respiratory assistance apparatus according to paragraph 1 wherein the ultrasound gas composition sensor system comprises a transmitter and receiver transducer pair that are operable to transmit cross-flow acoustic pulses from the transmitter to the receiver through the gases stream for sensing the speed of sound in the gases stream in the vicinity of the sensor assembly.

3. A respiratory assistance apparatus according to paragraph 2 wherein the transmitter and receiver transducer pair are arranged such that the acoustic pulses traverse the gases stream in a direction substantially perpendicular to the flow direction of the gases stream.

4. A respiratory assistance apparatus according to paragraph 2 wherein the transmitter and receiver transducer pair are arranged such that the acoustic pulses traverse the gases stream in a cross-flow that is angled but not perpendicular with respect to the flow direction of the gases stream.

5. A respiratory assistance apparatus according to any one of paragraphs 2-4 wherein the transmitter and receiver transducer pair comprises a transducer that is configured as a transmitter and a transducer that is configured as a receiver for transmitting uni-directional acoustic pulses.

6. A respiratory assistance apparatus according to any one of paragraphs 2-4 wherein the transmitter and receiver transducer pair comprises a pair of transmitter-receiver transducers that are configured for transmitting bi-directional acoustic pulses.

7. A respiratory assistance apparatus according to paragraph 5 or paragraph 6 wherein the transmitter and receiver are aligned with each other in relation to the flow direction of the gases stream and facing each other on opposite sides of the flow path.

8. A respiratory assistance apparatus according to paragraph 5 or paragraph 6 wherein the transmitter and receiver are displaced from each other in the flow direction of the gases stream.

9. A respiratory assistance apparatus according to paragraph 8 wherein the acoustic pulses have a beam path that is direct between the transmitter and receiver.

10. A respiratory assistance apparatus according to paragraph 8 wherein the acoustic pulses have a beam path that is indirect between the transmitter and receiver and which undergoes one or more reflections.

11. A respiratory assistance apparatus according to any one of paragraphs 2-4 wherein the transmitter and receiver transducer pair is in the form of a single transmitter-receiver that is configured to transmit cross-flow acoustic pulses and receive the echo return pulses.

12. A respiratory assistance apparatus according to paragraph 2 wherein the ultrasound gas composition sensor system comprises a transmitter and receiver transducer pair that are operable to transmit along-flow acoustic pulses from the transmitter to the receiver through the gases stream for sensing the speed of sound in the gases stream in the vicinity of the sensor assembly.

13. A respiratory assistance apparatus according to any one of paragraphs 2-12 further comprising a sensor control system that is operatively connected to the transmitter and receiver transducer pair of the ultrasound gas composition sensor system and which is configured to operate the transducer pair to sense and generate a speed of sound signal indicative of the speed of sound through the gases stream.

14. A respiratory assistance apparatus according to paragraph 13 wherein the sensor control system is configured to generate one or more gas concentration signals indicative of the gas concentration within the gases stream based at least on the signal indicative of the speed of sound though the gases stream.

15. A respiratory assistance apparatus according to paragraph 13 or paragraph 14 wherein the sensor assembly further comprises a temperature sensor that is configured to measure the temperature of the gases stream in the vicinity of the sensor assembly and generate a representative temperature signal, and wherein the sensor control system is configured to generate one or more gas concentration signals indicative of the gas concentration within the gases stream based on the speed of sound signal and the temperature signal.

16. A respiratory assistance apparatus according to paragraph 13 or paragraph 14 wherein the sensor assembly further comprises a humidity sensor that is configured to measure the humidity in the gases stream in the vicinity of the sensor assembly and generate a representative humidity signal, and wherein the sensor control system is configured to generate one or more gas concentration signals indicative of the gas concentration within the gases stream based on the speed of sound signal and the humidity signal.

17. A respiratory assistance apparatus according to paragraph 13 or paragraph 14 wherein the sensor assembly further comprises a temperature sensor that is configured to measure the temperature of the gases stream in the vicinity of the sensor assembly and generate a representative temperature signal and a humidity sensor that is configured to measure the humidity in the gases stream in the vicinity of the sensor assembly and generate a representative humidity signal, and wherein the sensor control system is configured to generate one or more gas concentration signals indicative of the gas concentration within the gases stream based on the speed of sound signal, temperature signal, and humidity signal.

18. A respiratory assistance apparatus according to paragraph 15 or paragraph 17 wherein the sensor control system is configured to apply a temperature correction to the temperature signal to compensate for any predicted temperature sensing error created by heat within the respiratory device that affects the temperature sensor.

19. A respiratory assistance apparatus according to paragraph 18 wherein the sensor assembly further comprises a flow rate sensor that is configured to sense the flow rate of the gases stream in the vicinity of the sensor assembly and generate a representative flow rate signal; and the system further comprises: a motor speed sensor being provided that is configured to sense the motor speed of the blower unit and generate a representative motor speed signal, and wherein the temperature correction is calculated by the sensor control system based at least on the flow rate signal and/or motor speed signal.

20. A respiratory assistance apparatus according to any one of paragraphs 13-19 wherein the sensor control system is configured to generate a gas concentration signal representing the oxygen concentration in the gases stream.

21. A respiratory assistance apparatus according to any one of paragraphs 13-19 wherein the sensor control system is configured to generate a gas concentration signal representing the carbon dioxide concentration in the gases stream.

22. A respiratory assistance apparatus according to any one of paragraphs 1-21 wherein the sensor assembly is releasably mounted within the flow path.

23. A respiratory assistance apparatus according to any one of paragraphs 1-22 wherein the flow path is shaped or configured to promote stable flow of the gases stream in at least one section or portion of the flow path.

24. A respiratory assistance apparatus according to paragraph 23 wherein the flow path is shaped or configured to promote stable flow in a section or portion of the flow path containing the sensor assembly.

25. A respiratory assistance apparatus according to paragraph 23 or paragraph 24 wherein the flow path comprises one or more flow directors at or toward the gases inlet.

26. A respiratory assistance apparatus according to paragraph 25 wherein each flow director is in the form of an arcuate fin.

27. A respiratory assistance apparatus according to any one of paragraphs 23-26 wherein the flow path comprises at least one spiral portion or section to promote stable flow of the gases stream.

28. A respirator assistance apparatus according to paragraph 27 wherein the flow path comprises an inlet section that extends between the gases inlet and the blower unit and the inlet section comprises at least one spiral portion.

29. A respiratory assistance apparatus according to paragraph 27 or paragraph 28 wherein the sensor assembly is located in a spiral portion of the flow path.

30. A respiratory assistance apparatus according to paragraph 29 wherein the spiral portion comprises one or more substantially straight sections, and the sensor assembly is located in one of the straight sections.

31. A respiratory assistance apparatus according to any one of paragraphs 2-30 wherein the sensor assembly comprises a sensor housing comprising a main body that is hollow and defined by peripheral walls that extend between a first open end and a second open end to thereby define a sensing passage in the main body between the walls through which the gases stream may flow in the direction of a flow axis extending between the first and second ends of the main body and wherein the transmitter and receiver transducer pair are located on opposite walls or sides of the sensing passage.

32. A respiratory apparatus according to paragraph 31 wherein the sensor housing comprises: a main body comprising two spaced-apart side walls, upper and lower walls extending between the side walls to define the sensing passage along the main body between its first and second ends; and a pair of transducer mounting assemblies located on opposing walls of the main body, which are each configured to receive and retain a respective transducer of the transducer pair such that they are aligned, and face each other, across the sensing passage of the main body.

33. A respiratory assistance apparatus according to any one of paragraphs 1-32 wherein the blower unit is operable to generate a gases stream at the gases outlet having a flow rate of up to 100 liters-per-minute.

34. A respiratory assistance apparatus according to any one of paragraphs 1-33 wherein the gases inlet is configured to receive a supply of gases comprising a mixture of atmospheric air and pure oxygen from an oxygen supply.

35. A respiratory assistance apparatus according to any one of paragraphs 1-33 wherein the gases inlet is configured to receive a supply of gases comprising a mixture of atmospheric air and carbon dioxide from a carbon dioxide supply.

36. A respiratory assistance apparatus according to any one of paragraphs 1-35 wherein the flow path is in the bulk flow path of the apparatus.

37. A sensor assembly for in-line flow path sensing of a gases stream in a respiratory assistance apparatus comprising: a sensor housing comprising a main body that is hollow and defined by peripheral walls that extend between a first open end and a second open end, to thereby define a sensing passage in the main body between the walls, through which the gases stream may flow in the direction of a flow axis extending between the first and second ends of the main body; an ultrasound gas composition sensor system mounted in the sensor housing for sensing one or more gas concentrations within the gases stream flowing in the sensing passage; a temperature sensor mounted in the sensor housing for sensing the temperature of the gases stream flowing in the sensing passage; and a flow rate sensor mounted in the sensor housing for sensing the flow rate of the gases stream flowing in the sending passage.

38. A sensor assembly according to paragraph 37 wherein the sensor housing is configured for releasable engagement into a complementary retaining aperture in the flow path of the respiratory assistance apparatus.

39. A sensor assembly according to paragraph 37 or paragraph 38 wherein the ultrasound gas composition sensor system comprises a transmitter and receiver transducer pair that are operable to transmit acoustic pulses from the transmitter to the receiver through the gases stream in a direction substantially perpendicular to the flow axis of the gases stream flowing through the sensing passage.

40. A sensor assembly according to paragraph 39 wherein the transmitter and receiver transducer pair are located on opposite walls or sides of the sensing passage.

41. A sensor assembly according to paragraph 39 or paragraph 40 wherein the main body of the sensor housing comprises two spaced-apart side walls, and upper and lower walls that extend between the side walls to define the sensing passage along the main body between its first and second ends; and a pair of transducer mounting assemblies located on opposing walls of the main body, which are each configured to receive and retain a respective transducer of the transducer pair such that they are aligned, and face each other, across the sensing passage of the main body.

42. A sensor assembly according to paragraph 41 wherein the pair of transducer mounting assemblies are located on opposite side walls of the main body, and wherein each transducer mounting assembly comprises a retaining cavity within which a respective transducer of the pair are received and retained.

43. A sensor assembly according to paragraph 42 wherein each transducer mounting assembly comprises a cylindrical base portion that extends from a respective side wall of the main body and at least one pair of opposed clips that extend from the base portion, the base portion and clips collectively defining the retaining cavity.

44. A sensor assembly according to paragraph 43 wherein each side wall of the main body comprises a transducer aperture which is co-aligned with its associated transducer mounting assembly and through which the front operating face of the transducer may extend to access the sensing passage.

45. A sensor assembly according to paragraph 44 wherein the transducer mounting assemblies are configured to locate their respective transducers such that the operating faces of the transducers are substantially flush with the inner surface of their respective wall of the main body of the sensor housing.

The foregoing description of the invention includes preferred forms thereof. Modifications may be made thereto without departing from the scope of the invention as defined by the accompanying claims.

The invention claimed is:

1. A respiratory assistance apparatus configured to provide a heated and humidified gases stream, comprising:
   a gases inlet configured to receive a supply of gases;
   a blower unit configured to generate a pressurised gases stream from the supply of gases;
   a humidification unit configured to heat and humidify the pressurised gases stream;
   a gases outlet for the heated and humidified gases stream;
   a flow path for the gases stream through the respiratory assistance apparatus from the gases inlet through the blower unit and humidification unit to the gases outlet;
   a sensor assembly provided in the flow path before the humidification unit such that the sensor assembly is configured to sense one or more characteristics of a bulk flow of the gases stream, the sensor assembly comprising an ultrasound gas composition sensor system and a temperature sensor, wherein the ultrasound gas composition sensor system comprises a transmitter and a receiver, the transmitter and receiver forming a transmitter and receiver transducer pair that are operable to transmit cross-flow or along-flow acoustic pulses from the transmitter to the receiver through the gases stream to measure a speed of sound in the gases stream in the vicinity of the sensor assembly, and wherein the temperature sensor is configured to measure a temperature of the gases stream in the vicinity of the sensor assembly and generate a representative temperature signal; and
   a sensor control system operatively connected to the transmitter and receiver of the ultrasound gas composition sensor system, wherein the sensor control system is configured to operate the transmitter and receiver transducer pair to measure the speed of sound in the gases stream and generate a speed of sound signal and configured to calculate one or more gas concentrations within the gases stream using the speed of sound signal and the representative temperature signal,
   wherein the sensor assembly comprises a housing comprising a hollow main body, wherein the flow path passes through the main body, the housing further comprising mounting assemblies configured to retain the transmitter and receiver, and wherein the temperature sensor is mounted to the main body.

2. A respiratory assistance apparatus according to claim 1 wherein the transmitter and receiver transducer pair are arranged such that the acoustic pulses traverse the gases stream in a direction substantially perpendicular to a flow direction of the gases stream.

3. A respiratory assistance apparatus according to claim 1 wherein the transmitter and receiver transducer pair are arranged such that the acoustic pulses traverse the gases stream in a cross-flow that is angled but not perpendicular with respect to the flow direction of the gases stream.

4. A respiratory assistance apparatus according to claim 1 wherein the transmitter and receiver transducer pair comprises a transducer that is configured as a transmitter and a transducer that is configured as a receiver for transmitting uni-directional acoustic pulses.

5. A respiratory assistance apparatus according to claim 4 wherein the transmitter and receiver are aligned with each other in relation to a flow direction of the gases stream and facing each other on opposite sides of the flow path.

6. A respiratory assistance apparatus according to claim 4 wherein the transmitter and receiver are displaced from each other in a flow direction of the gases stream.

7. A respiratory assistance apparatus according to claim 6 wherein the acoustic pulses have a beam path that is direct between the transmitter and receiver.

8. A respiratory assistance apparatus according to claim 6 wherein the acoustic pulses have a beam path that is indirect between the transmitter and receiver and which undergoes one or more reflections.

9. A respiratory assistance apparatus according to claim 1 wherein the transmitter and receiver transducer pair comprises a pair of transmitter-receiver transducers that are configured for transmitting bi-directional acoustic pulses.

10. A respiratory assistance apparatus according to claim 9 wherein the transmitter and receiver are aligned with each other in relation to a flow direction of the gases stream and facing each other on opposite sides of the flow path.

11. A respiratory assistance apparatus according to claim 9 wherein the transmitter and receiver are displaced from each other in a flow direction of the gases stream.

12. A respiratory assistance apparatus according to claim 11 wherein the acoustic pulses have a beam path that is direct between the transmitter and receiver.

13. A respiratory assistance apparatus according to claim 11 wherein the acoustic pulses have a beam path that is indirect between the transmitter and receiver and which undergoes one or more reflections.

14. A respiratory assistance apparatus according to claim 1 wherein the transmitter and receiver transducer pair is in the form of a single transmitter-receiver that is configured to transmit cross-flow acoustic pulses and receive echo return pulses.

15. A respiratory assistance apparatus according to claim 1 wherein the sensor assembly further comprises a humidity sensor that is configured to measure the humidity in the gases stream in the vicinity of the sensor assembly and generate a representative humidity signal, and wherein the sensor control system is configured to generate one or more gas concentration signals indicative of the gas concentration within the gases stream using the speed of sound signal and the representative humidity signal.

16. A respiratory assistance apparatus according to claim 1 wherein the sensor control system is configured to generate a gas concentration signal representing oxygen concentration in the gases stream.

17. A respiratory assistance apparatus according to claim 1 wherein the sensor control system is configured to generate a gas concentration signal representing carbon dioxide concentration in the gases stream.

18. A respiratory assistance apparatus according to claim 1 wherein the hollow main body is defined by peripheral walls that extend between a first open end and a second open end to thereby define a sensing passage in the main body between the walls through which the gases stream may flow in the direction of a flow axis extending between the first and second ends of the main body and wherein the transmitter and receiver transducer pair are located on opposite walls or sides of the sensing passage.

19. A respiratory apparatus according to claim 18 wherein the mounting assemblies are located on opposing walls of the main body, which are each configured to receive and retain a respective transducer of the transmitter and receiver transducer pair such that they are aligned, and face each other, across the sensing passage of the main body.

20. A respiratory assistance apparatus according to claim 1, wherein the temperature sensor is separated from a wall at least partially defining the flow path and is suspended into the gases stream.

21. A respiratory assistance apparatus according to claim 1, wherein the sensor assembly is releasbly mounted in the flow path.

* * * * *

UNITED STATES PATENT AND TRADEMARK OFFICE
CERTIFICATE OF CORRECTION

PATENT NO. : 10,357,629 B2
APPLICATION NO. : 14/390358
DATED : July 23, 2019
INVENTOR(S) : Dean Antony Barker Page 1 of 1

It is certified that error appears in the above-identified patent and that said Letters Patent is hereby corrected as shown below:

In the Specification

Column 18, Line 10, change "thermister" to --thermistor--.

In the Claims

Column 33, Line 21, in Claim 21, change "releasbly" to --releasably--.

Signed and Sealed this
Twenty-ninth Day of October, 2019

Andrei Iancu
*Director of the United States Patent and Trademark Office*